US008913078B2

(12) United States Patent
Masumoto

(10) Patent No.: US 8,913,078 B2
(45) Date of Patent: Dec. 16, 2014

(54) DIAGNOSIS ASSISTING SYSTEM, COMPUTER READABLE RECORDING MEDIUM HAVING DIAGNOSIS ASSISTING PROGRAM RECORDED THEREON, AND DIAGNOSIS ASSISTING METHOD

(75) Inventor: Jun Masumoto, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 793 days.

(21) Appl. No.: 12/881,892

(22) Filed: Sep. 14, 2010

(65) Prior Publication Data
US 2011/0105879 A1 May 5, 2011

(30) Foreign Application Priority Data

Sep. 15, 2009 (JP) ................................. 2009-212652
Mar. 31, 2010 (JP) ................................. 2010-084280

(51) Int. Cl.
*G09G 5/00* (2006.01)
*G06F 19/00* (2011.01)

(52) U.S. Cl.
CPC .......... *G06F 19/321* (2013.01); *G06F 19/3487* (2013.01); *G06F 19/3443* (2013.01)
USPC ........................................................ 345/619

(58) Field of Classification Search
None
See application file for complete search history.

(56) References Cited

U.S. PATENT DOCUMENTS

| | | | |
|---|---|---|---|
| 7,058,901 B1 * | 6/2006 | Hafey et al. .................... | 715/792 |
| 7,646,903 B2 | 1/2010 | Kaftan et al. | |
| 8,019,626 B2 * | 9/2011 | Mahesh et al. .................... | 705/3 |
| 2003/0016853 A1 * | 1/2003 | Oosawa ........................ | 382/132 |
| 2005/0259116 A1 * | 11/2005 | Araoka ......................... | 345/619 |
| 2007/0242069 A1 * | 10/2007 | Matsue et al. ................ | 345/428 |
| 2007/0245267 A1 * | 10/2007 | Nakamura et al. ........... | 715/838 |
| 2008/0212854 A1 | 9/2008 | Fukatsu et al. | |
| 2009/0080744 A1 * | 3/2009 | Sagawa ......................... | 382/131 |
| 2009/0232378 A1 | 9/2009 | Nakamura | |
| 2010/0077330 A1 * | 3/2010 | Kaplan et al. ................. | 715/764 |

FOREIGN PATENT DOCUMENTS

| | | |
|---|---|---|
| JP | 2004160103 A | 6/2004 |
| JP | 2005-28121 A | 2/2005 |
| JP | 2007-29248 A | 2/2007 |
| JP | 2007275216 A | 10/2007 |
| JP | 2008022918 A | 2/2008 |
| JP | 2008200139 A | 9/2008 |
| JP | 2009148422 A | 7/2009 |

OTHER PUBLICATIONS

D. Rueckert, et al., "Nonrigid Registration Using Free-Form Deformations: Application to Breast MR Images", IEEE Transactions on Medical Imaging, Aug. 1999, pp. 712-721, vol. 18, No. 8.
Japanese Office Action issued Aug. 13, 2013 in corresponding Japanese Patent Application No. 2010-084280.

* cited by examiner

*Primary Examiner* — Phi Hoang
*Assistant Examiner* — Mohammad H Akhavannik
(74) *Attorney, Agent, or Firm* — Sughrue Mion, PLLC

(57) ABSTRACT

A plurality of images for observation in different observation formats and thumbnail images corresponding to each image for observation are generated from volume data obtained for the same subject on different imaging dates/times. A plurality of image windows, which can be switched between an active state and an inactive state, are arranged on a diagnosis screen, and images for observation generated from volume data obtained on specified imaging dates are displayed in each image window. In one embodiment, thumbnail images having the same observation format as an image for observation are displayed in the vicinity of the image for observation within an image window in the active state.

26 Claims, 17 Drawing Sheets

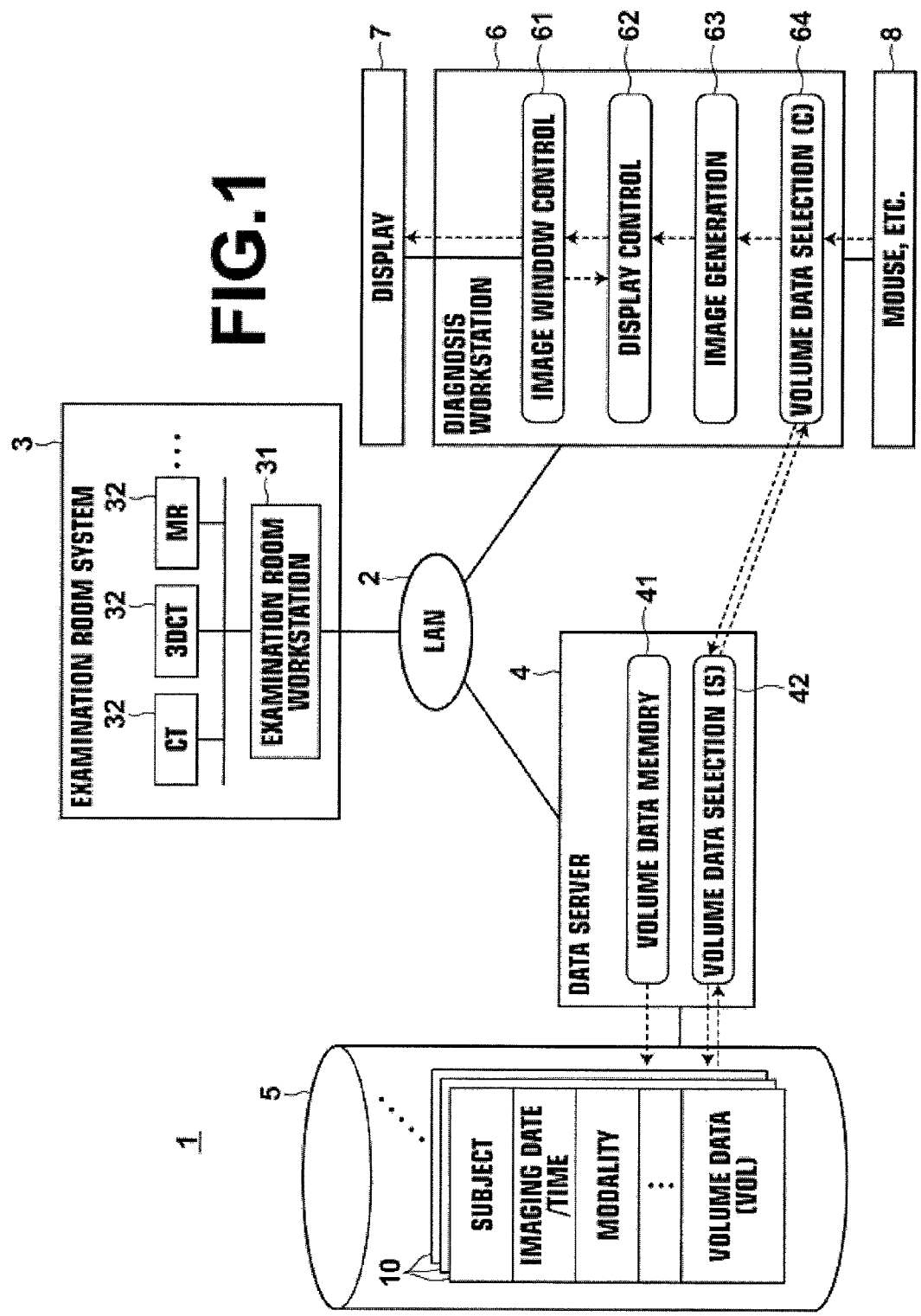

DIAGNOSIS ASSISTING SYSTEM, COMPUTER READABLE RECORDING MEDIUM HAVING DIAGNOSIS ASSISTING PROGRAM RECORDED THEREON, AND DIAGNOSIS ASSISTING METHOD

BACKGROUND OF THE INVENTION

1. Field of the Invention

The present invention is suited for utilization in the medical field, and is related to a system and a method for assisting image diagnosis using three dimensional image data. The present invention is also related to a computer readable recording medium having a diagnosis assisting computer program stored thereon.

2. Description of the Related Art

In image diagnosis, there are cases in which images of a subject obtained during recent examinations (hereinafter, referred to as "current images") are compared against images of the same subject obtained in previous examinations (hereinafter, referred to as "past images"), to confirm changes in symptoms of disease (hereinafter, referred to as "comparative image observation"). For this reason, many diagnosis assisting apparatuses are equipped with the function of selecting past images that represent the same position of a subject within an image which is currently being observed from a database of past images, and displaying the selected past images along with the observed current image.

A common user interface for comparative image observation displays a current image and a past image of the same size alongside each other on the screen of a monitor. An example of such a user interface is illustrated in FIG. 9, FIG. 11, and FIG. 12 of U.S. Patent Application Publication No. 20090080744. These figures illustrate screens of monitors, on which current images and past images having the same slice positions are displayed alongside each other during comparison of slice images obtained by a CT apparatus or the like. In addition, FIG. 15 of this document illustrates a case in which the contents of display of the monitor screen are switched between a current image and a past image by a scrolling operation. Further, a system in which two or more monitors are connected to a diagnosis assisting apparatus, a group of current images is displayed on one monitor, and groups of past images are displayed on one or a plurality of other monitors, is also proposed.

As another example of a user interface for comparative image observation is that in which only the regions of interest within two images are displayed close to each other (refer to FIG. 8, FIG. 9, FIG. 13, and FIG. 14 of Japanese Unexamined Patent Publication No. 2007-029248).

When using an interface that displays current images and past images alongside each other on the screen of a single monitor or on the screens of a plurality of monitors, physicians who observe the images must view the images while moving their lines of sight vertically and horizontally. Particularly in systems which are equipped with three or more monitors that are arranged vertically and horizontally, there are cases in which the physicians' heads must be rotated in addition to changing their lines of sight. These interfaces are likely to cause fatigue of the eyes and sore shoulders. On the other hand, when using an interface that switches between display of a current image and a past image by a scrolling operation, physicians must perform comparisons while one of the images is not within their fields of view (while retaining one of the images within their memories). This type of operation exerts a burden on the physicians' brains, and is likely to cause nervous fatigue.

Japanese Unexamined Patent Publication No. 2007-029248 proposes to reduce the amount of line of sight movement by displaying only the regions of interest close to each other. However, this document is silent regarding an image layout for cases in which a plurality of examinations have been performed in the past, and there is a great number of images to be compared.

The present invention has been developed in view of the foregoing circumstances. It is an object of the present invention to provide a user interface that reduces physical/mental fatigue of physicians that perform image observation.

A diagnosis assisting system of the present invention is a system equipped with a volume data storage means, a volume data selecting means, an image generating means, an image window control means, and a display control means, to be described below. In addition, a computer readable recording medium, on which a diagnosis assisting program of the present invention is recorded, causes one or a plurality of computers to function as the volume data selecting means, the image generating means, the image window control means, and the display control means, to be described below. The diagnosis assisting program of the present invention is constituted by a plurality of program modules. The functions of each of the aforementioned means are realized by one or a plurality of program modules. The group of program modules is provided to users by being recorded in storage media such as CD-ROM's and DVD's, by being recorded in a storage unit attached to a server computer in a downloadable state, or by being recorded in network storage in a downloadable state. A diagnosis assisting method of the present invention is a method that assists diagnosis, by causing a single computer or a plurality of computers to execute the processes of the volume data storage means, the volume data selecting means, the image generating means, the image window control means, and the display means, to be described later.

The volume data storage means stores a plurality of sets of volume data, obtained by imaging at least one subject on different imaging dates/times, in a predetermined storage device, correlated with subject identifying data and imaging date/time data. The storage device may be an internal memory or a storage of a computer that constitutes the diagnosis assisting system, an external storage device which is connected to the computer either directly or via a network, or the like.

Note that the term "subject" refers to a target of examination, that is, a portion which is the target of imaging and diagnosis. For example, in the case that the lungs and the stomach of a single patient are examined, there are two subjects, although there is only one patient. In this case, it is preferable for the subject identifying data to include both patient data and imaged portion data.

The volume data selecting means selects at least two sets of volume data correlated with subject identifying data that represents a specified subject, from among the sets of volume data stored in the storage device. Thereby, a plurality of sets of volume data regarding the same subject obtained on different imaging dates/times are obtained. For example, in the case that three CT examinations are performed on a subject, three sets of volume data, each of which is obtained at each examination, are obtained. Note that in cases that a plurality of sets of volume data are obtained by performing imaging using a plurality of modalities on a single imaging date, or by performing a plurality of imaging operations in temporal series during a single examination, there is a possibility that two or more sets of volume data are selected for a single imaging date.

The image generating means generates a plurality of images for observation in different observation formats that represent the specified subject for each set of volume data selected by the volume data selecting means, and generates a plurality of thumbnail images corresponding to each of the images for observation. The image generating means also correlates the images for observation, the thumbnail images, and the imaging date/time data of the set of volume data corresponding thereto. It is preferable for a positioning process to be performed such that the position of the subject within the images for observation and the thumbnail images generated from each set of volume data are matched among sets of volume data, when generating the images for observation and the thumbnail images. The positioning process may be administered onto the volume data, or onto the generated images for observation and the generated thumbnail images.

Note that the expression "different observation formats" refers to differences in the method of representation by which the subject is represented. That is, the portion of the subject which is focused on and how this portion is presented to a user differ. For example, images that are converted from volume data to two dimensional images by different conversion methods (the volume rendering method, the multi planar reconstruction method, etc.) are images having different observation formats. In addition, even if the conversion method is the same, images having different conversion parameters (viewpoint, direction of view, slice position, etc.) are images having different observation formats.

The image window control means arranges a plurality of image windows, which are switchable between an active state and an inactive state, on a screen, and controls the switching from the active state and the inactive state. Here, the active state refers to a state in which operational input can be received with respect to the contents displayed within an image window, and the inactive state refers to a state in which operational input cannot be received with respect to the contents displayed within an image window. The plurality of image windows may be windows that can be placed such that they overlap each other as necessary at a desired position on a display screen, or may be regions that the display screen is divided into. Further, it is preferable for the image window control means to be able to change the layout of the plurality of image windows in response to predetermined user operations.

The display control means selects images for observation which are correlated with imaging date/time data that represent a specified imaging date/time from among the images for observation generated by the image generating means, and displays the selected images for observation in the image windows. Here, the "specified date/time" needs only to specify a range of year/month/day/hour/minute/second which is sufficient to enable selection of images for observation. With regard to the selection of images for observation, in the case that a VR image and three MPR images corresponding to three cross sections are generated as the images for observation, the VR image and the three MPR images are each displayed within one of four image windows, for example.

Further, the display control means selects thumbnail images having the same observation format as that of the image for observation which is displayed in the active image window from among the thumbnail images generated by the image generating means, and displays the selected thumbnail images within the active image window. Having the same observation format refers to the subject being represented by the same method of representation. That is, having the same observation format refers to the aforementioned conversion method and the conversion parameters of the images being the same.

In the aforementioned structures and procedures, images which are targets for comparison do not appear on the screen, unless the image window that the image is displayed within is switched to the active state. For this reason, comparative image observation can be performed without confusion, even when a plurality of images for observation having different observation formats are displayed on the screen of a monitor. In addition, because the images to be compared are displayed as thumbnail images within a single image window, it becomes possible to compare the images without moving lines of sight greatly, even in cases that there is a great number if images to be compared. In addition, the need to prepare a plurality of monitors to perform comparative image observation is obviated.

However, during actual diagnosis, there are cases in which it is desired to comparatively observe only images obtained during a specific time period. For example, assuming that all of the results of periodic physical examinations are stored, there are cases in which it is desired to exclude images prior to an abnormality appearing and to use only images obtained after the abnormality was discovered, when performing comparative image observation. Alternatively, in the case that the number of images of a single subject is inordinately great due to series of examinations being performed over a long period of time or at high frequency, or due to images being obtained at a plurality of points in time accompanying ingestion of imaging agents, it is practically impossible to perform comparative image observation of all of the images. In such cases, it may be desired to narrow down the images when performing comparative image observation. The present invention proposes the following two means in response to such needs.

A first means is to configure the volume data selecting means such that it selects volume data that satisfies first narrowing conditions, to narrow sets of volume data which are targets for selection. Thereby, sets of volume data which are correlated with subject identifying data of a specified subject but do not satisfy the first narrowing conditions are not selected. Images for observation and thumbnail images are not generated from the sets of volume data which are not selected, and the display control means is enabled to display only images that comparative image observation is desired to be performed on. In addition, because only images that comparative image observation is desired to be performed on are generated, the processing load on the system is reduced, and processing efficiency is improved.

More specifically, the first narrowing conditions may be those that narrow the volume data to be selected to volume data which were obtained by imaging within a predetermined period. In this case, the volume data selecting means selects sets of volume data that satisfy the first narrowing conditions, based on the imaging date/time data correlated with the volume data. Alternatively, the volume data stored in the storage device may be further correlated with examination identifying data that identify each examination by which volume data were obtained, and the first narrowing conditions may be those that narrow the volume data to be selected to volume data which were obtained by a predetermined number of recent examinations. In this case, the volume data selecting means selects sets of volume data that satisfy the first narrowing conditions, based on the examination identifying data correlated with the volume data. As a further alternative, the volume data stored in the storage device may be further correlated with one of examination data that represent the examination during obtainment of the volume data and diagnostic result data that represent the results of diagnosis, and the first narrowing conditions may be those that narrow volume data to be selected to volume data which are correlated with one of a specific examination and a specific diagnostic result. In this case, the volume data selecting means selects sets of volume data that satisfy the first narrowing conditions, based on the examination data and the diagnostic result data correlated with the volume data. Here, the "specific examination or specific diagnostic result" refers to an examination results that indicate an abnormality, or a diagnosis indicating a specific disease.

A second means is to configure the display control means such that it selects thumbnail images that further satisfy second narrowing conditions, and causes the selected thumbnail images to be displayed within an image window in the active state. Thereby, thumbnail images having the same observation format as an image for observation which is displayed within an active image window but do not satisfy the second narrowing conditions are not selected as display targets. Therefore, only images that comparative image observation is desired to be performed on can be displayed. In addition, in this second means, the images for observation and the thumbnail images are generated even for those that do not satisfy the second narrowing conditions. Therefore, if the second narrowing conditions are changed or lifted, images which had previously not been targets for comparative image observation will be immediately available for display.

More specifically, the second narrowing conditions may be those that narrow the thumbnail images to be selected to thumbnail images which were obtained by imaging within a predetermined period. In this case, the display control means selects thumbnail images that satisfy the second narrowing conditions, based on the imaging date/time data correlated with the thumbnail images. That is, during selection of thumbnail images by the display control means, thumbnail images having the same observation format as an image for observation which is displayed in an active image window and correlated to imaging date/time data that represents an imaging date/time within the specified period are selected. Alternatively, the volume data stored in the storage device may be further correlated with examination identifying data that identify each examination by which volume data were obtained, the image generating means may correlate the examination identifying data, which are correlated to the volume data, to the images for observation and the thumbnail images generated therefrom, and the second narrowing conditions may be those that narrow the thumbnail images to be selected to be those which are generated from volume data which were obtained by a predetermined number of recent examinations. In this case, the display control means selects and displays thumbnail images that satisfy the second narrowing conditions, based on the examination identifying data correlated with the thumbnail images. As a further alternative, the volume data stored in the storage device may be further correlated with one of examination data that represent the examination during obtainment of the volume data and diagnostic result data that represent the results of diagnosis, the image generating means may correlate the examination data and the diagnostic result data, which are correlated to the volume data, to the images for observation and the thumbnail images generated therefrom, and the second narrowing conditions may be those that narrow volume data to be selected to volume data which are correlated with one of a specific examination and a specific diagnostic result. In this case, the display control means selects and displays thumbnail images that satisfy the second narrowing conditions, based on the examination data and the diagnostic result data correlated with the thumbnail images.

Alternatively, the display control means may receive settings regarding a maximum value for the number of thumbnail images to be displayed within an image window in the active state, and display a number of thumbnail images less than or equal to the set maximum value, regardless of whether the thumbnail images are narrowed as described above. Thereby, the displayed thumbnail images becoming too small and difficult to view due to the number thereof increasing can be prevented. Further, the display control means may receive selection of thumbnail images to be displayed, and display only the selected thumbnail images, in the case that the number of selected thumbnail images exceeds the maximum value. Thereby, it becomes possible to display only thumbnail images that a user desires to view.

As a further alternative, the display control means may receive settings regarding whether each of the thumbnail images within an image window in the active state are to be displayed, and only display thumbnail images which are set to be displayed. Thereby, it becomes possible for users to cause selective display of only thumbnail images that they wish to view. Further, the display control means may display positions at which thumbnail images, which have been set to not be displayed, had been displayed in a recognizable manner. By adopting this configuration, users will be enabled to be aware of the presence of the thumbnail images that were set not to be displayed, thereby preventing necessary images from being overlooked.

A configuration may be adopted, wherein the display control means displays a catalog of images for observation that correspond to thumbnail images which are displayed within an image window in the active state, in response to a predetermined operation by a user. By adopting this configuration, detailed comparative image observation can be performed using images for observation of large sizes, even in cases that the sizes of individual thumbnail images are too small and cause comparative image observation to become difficult, by the catalog of corresponding images for observation being displayed.

It is common for images to be observed while switching observation formats on a diagnosis screen, in image diagnosis employing volume data. Accordingly, it is preferable for the image generating means to generate an image for observation and a thumbnail image corresponding to a specified observation format, when an operation that requests a change in the observation format of an image for observation displayed in an active image window, and for the display control means to update the display to display the generated image for observation and the generated thumbnail image. It is particularly preferable for the updating of the image for observation and the thumbnail image to be performed synchronously, such that the observation formats of the images to be compared can be switched in a coordinated manner as a whole.

Note that a preferred specific example of an operation that requests a change in the observation format is an operation that specifies a region to be cut out within an image for observation which is displayed within an active image window. In this case, the image generating means generates a thumbnail image corresponding to the region which is to be cut out. Then, the display control means displays the region to be cut out within the image for observation in a recognizable format, and updates the display to display the generated thumbnail image.

The thumbnail images may be displayed within image windows in the active state such that they are overlapped on the edges of an image for observation, which had been being displayed also during the inactive state. Alternatively, an image for observation, which had been being displayed within an image window in the inactive state, may be reduced in size, and the thumbnail images may be arranged within the space created by the size reduction. However, there is a possibility that the image for observation becomes difficult to observe in an image window in the active state than in an image window in the inactive state, if these layouts are applied. Therefore, it is preferable for the display to be controlled such that the thumbnail images are arranged about the periphery of an image for observation, which had been being displayed from during the inactive state, when the image window in which the image for observation is displayed is switched to the active state.

For example, a configuration may be adopted, wherein:

the image window control means arranges a plurality of image windows having one constant display region and at least one temporary display region on the screen, and controls each image window such that the temporary display regions appear on the screen only when the image window it belongs in is in an active state. The constant display region is a region which is displayed regardless of whether the image window that it belongs to is in the active state or the inactive state. The temporary display regions are regions which are temporarily displayed only when the image window that it belongs to is in the active state. It is preferable for the temporary display regions to be set based on the number of selected thumbnail images or the like. It is also preferable for the temporary display regions to be of sizes such that they are within the field of view of a user with the constant display region.

By configuring the image windows as described above, displaying the selected images for observation within the constant display regions of the image windows, and displaying the selected thumbnail images in the temporary display regions of an image window in the active state, it appears to a user that an image window expands and the thumbnail images are displayed in the vicinity of the image for observation, when the image window is switched to the active state.

Note that it is preferable for the display control means to display an image for observation within the constant display region of an active image window corresponding to a specified thumbnail image, when a first operation that specifies a thumbnail image within a temporary display region is detected. By adopting this configuration, a user can sequentially perform the first operation with respect to a plurality of thumbnail images which are displayed in the temporary display regions, and observe each image in detail.

In addition, it is preferable for the display control means to replace a specified thumbnail image within a temporary display region with an image for observation corresponding to the specified thumbnail image, when a second operation that specifies a thumbnail image within a temporary display region is detected. By adopting this configuration, the image which is displayed within the constant display region and the image specified by a user are displayed as images for observation of the same size, and comparison of the two images is facilitated.

Further, it is preferable for the display control means to add and display the photography date represented by the photography date/time data correlated to each of the images for observation and/or the thumbnail images when displaying the images for observation and/or the thumbnail images. By adopting this configuration, confirmation of the imaging date/time of images during comparative image observation is facilitated.

According to the diagnosis assisting system, the diagnosis assisting method, and the computer readable recording medium on which the diagnosis assisting program of the present invention is recorded, a plurality of types of images are displayed on a diagnosis screen. Even in the case that a plurality of examinations has been performed in the past, and the number of images to be comparatively observed is great, users can perform comparative image observation with little fatigue.

BRIEF DESCRIPTION OF THE DRAWINGS

FIG. 1 is a diagram that illustrates the schematic structure of a diagnosis assisting system according to an embodiment of the present invention.

DESCRIPTION OF THE PREFERRED EMBODIMENTS

Figure 2A:
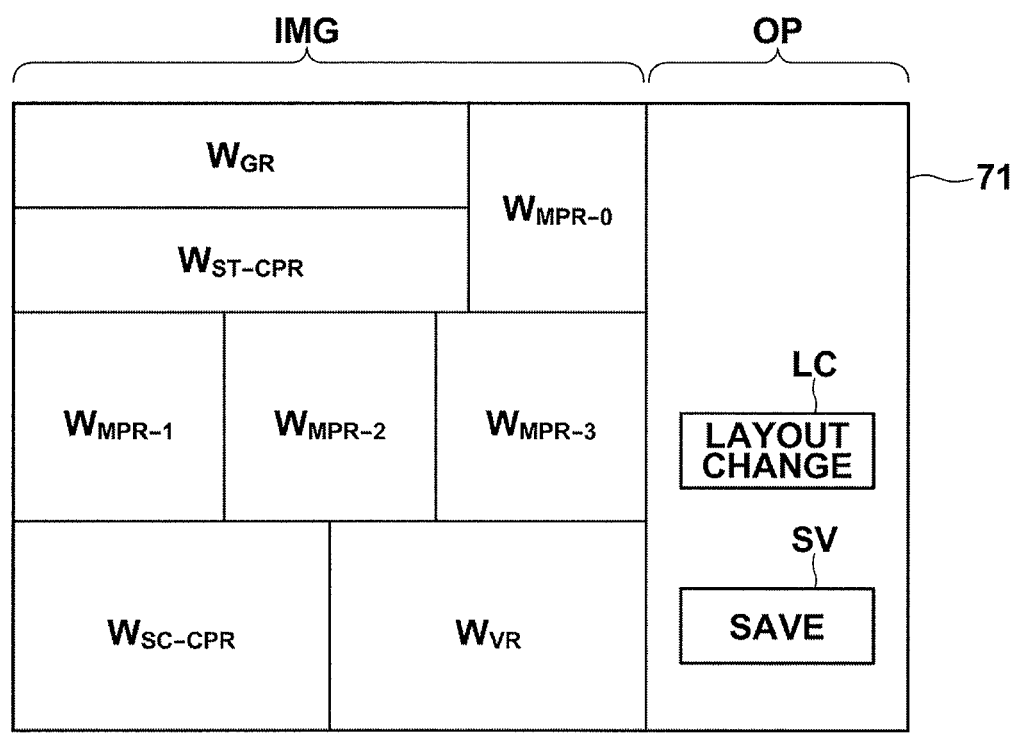
FIG. 2A is a diagram that illustrates a first example of the layout of a diagnosis screen.

FIG. 1 illustrates the schematic structure of a diagnosis assisting system according to an embodiment of the present invention. The diagnosis assisting system of the present embodiment is constituted by: an examination room system 3; a data server 4; and a diagnosis workstation 6 (WS 6); which are connected to each other via a local area network 2 (LAN 2).

The examination room system 3 is constituted by: a modality group 32 for imaging subjects; and an examination room workstation 31 (WS 31) for confirming and adjusting images output from each modality.

In the case that the modality 32 is that which outputs two dimensional slice data (such as a CT (Computed Tomography) apparatus and an MR (Magnetic Resonance) apparatus), the examination room WS 31 reconstructs the groups of slice data to generate three dimensional volume data, and sends the generated volume data to the data server 4 along with appended data. In the case that the modality 32 is that which directly outputs volume data (such as a 3DCT apparatus and a cone beam CT apparatus), the examination room WS 31 sends the volume data to the data server 4 along with appended data.

The data server 4 is a comparatively high processing performance computer equipped with a high performance processor and a high capacity memory, in which a software program that provides the functions of a DBMS (Database Management Server) is installed. The program is stored in a storage, loaded into the memory when the computer is booted up, and executed by the processor. Thereby, the data server 4 functions as a volume data storage means 41 and as a volume data selecting means 42 on a server side (S).

The volume data storage means 41 causes the volume data and the appended data sent from the examination room WS 31 to be stored in a high capacity storage, which is connected to the data server 4, as files 10. Each of the files 10 includes a header region and a region in which the volume data are stored. The appended data which are sent from the examination room WS 31, and appended data to be used for data searching which the data server 4 adds are stored in the header region. For example, data that represent a patient ID number, name, age, sex, and imaged portions (head, chest, abdomen) are stored as data that specify subjects. In addition, data regarding the dates on which imaging was performed, and data regarding the times at which imaging was performed are stored as data that specify imaging dates/times. Further, data regarding the modality which was utilized for imaging, data regarding imaging conditions (whether an imaging agent was used, the pigment which was used, the radionuclide, the radiation dosage, etc.) are stored.

Note that the volume data which are stored in the high capacity storage 5 as files may be volume data output from imaging modalities as they are, or volume data obtained by reconstituting data (such as slice data) output from imaging modalities. Further, the volume data which are stored in the high capacity storage 5 may be volume data which has been processed, such as to remove data unnecessary for diagnosis from the volume data obtained by imaging.

The volume data selecting means 42 selects files that satisfy search conditions from among the plurality of files 10 stored in the high capacity storage 5, in response to search requests from the diagnosis WS 6. Then, the volume data selecting means 42 sends the selected files to the diagnosis WS 6.

The diagnosis WS 6 is a general purpose workstation equipped with a normal processor and memory, in which programs that provide each of the functions to be described below are loaded. The programs are stored in the memory, and executed by the processor. By adopting this configuration, the diagnosis WS 6 functions as an image window control means 61, a display control means 62, an image generating means 63, and a volume data selecting means 64 on the client side (C). In addition, a display 7, and input devices 8 such as a keyboard and mouse are connected to the diagnosis WS 6.

Hereinafter, the functions, structure, and operations of the diagnosis WS 6 will be described further. The diagnosis WS 6 provides a variety of diagnosis assisting functions according to the type of tissue which is the target of diagnosis (organs, bones, muscles, blood vessels, etc.). The present invention is applicable regardless of the target of diagnosis. However, here, a case in which a function for assisting diagnosis of coronary arteries is selected will be described as an example.

First, the functions of the diagnosis WS 6 (mainly the user interface) will be described. If the function for assisting diagnosis of coronary arteries is selected in an initial screen, a dialog box for entering or selecting a value that specifies a patient (an ID number or the like), a value that represents an imaging date/time, and a value that specifies a reference time period for performing comparative image observation appears. When a subject (patient and portion) and an imaging date/time are specified by user input or selection operations, a diagnosis screen that represents images of the coronary arteries of the specified subject on the specified imaging date and time is displayed.

Figure 2B:
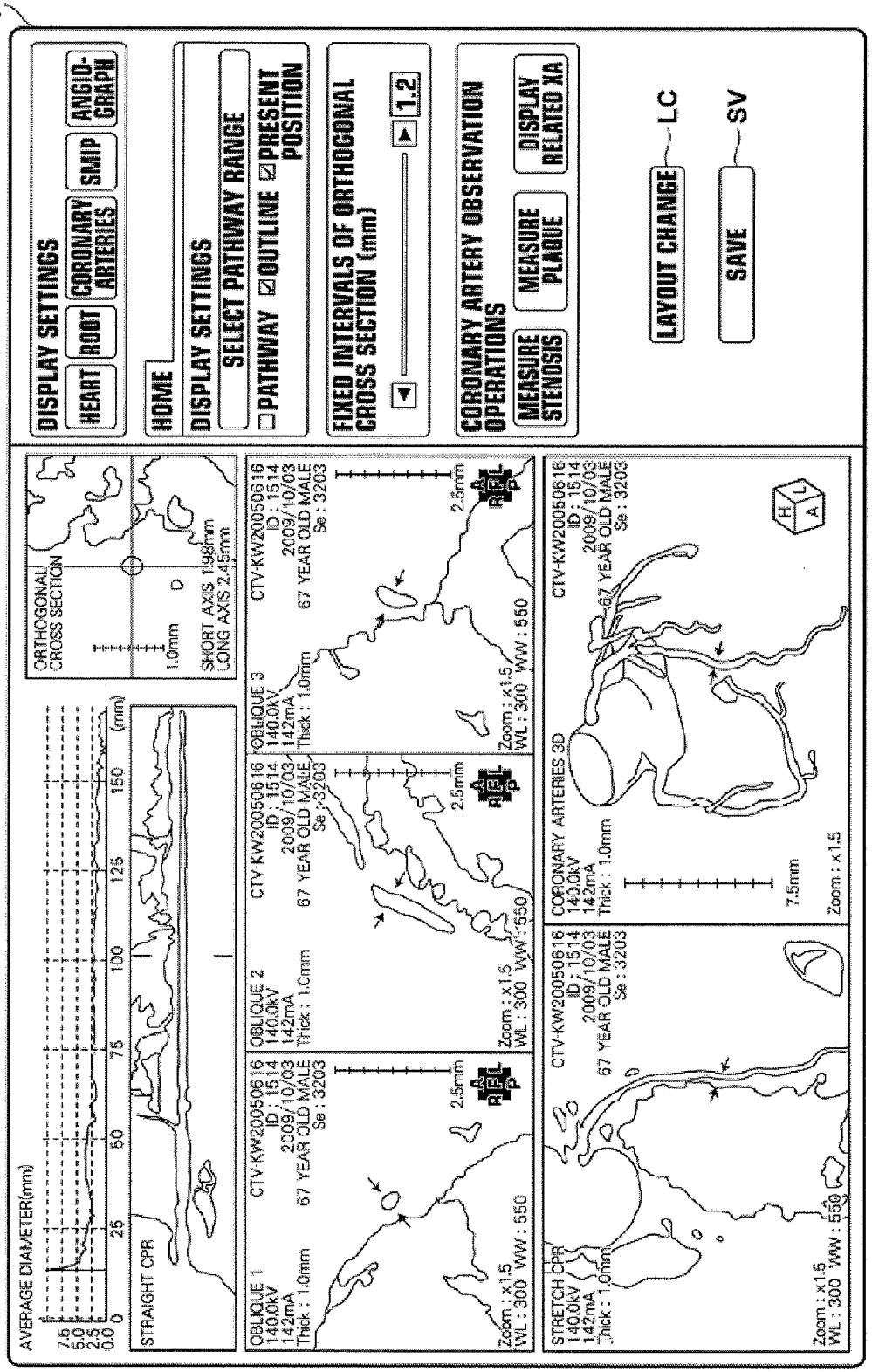
FIG. 2B is a diagram that illustrates an example of a diagnosis screen display.

FIG. 2A and FIG. 2B illustrate examples of diagnosis screens for coronary arteries. FIG. 2A is a diagram that illustrates an image layout of a diagnosis screen 71 which is displayed on the display 7. FIG. 2B is a diagram that illustrates a specific example of the display of the diagnosis screen 71. As illustrated in FIG. 2A, the diagnosis screen is sectioned into an image region IMG, within which a plurality of image windows are arranged, and an operating region OP, in which operating buttons and the like for switching screens and adjusting images are arranged.

A plurality of image windows are arranged within the image region IMG. FIG. 2A illustrates eight image windows, including: a window $W_{GR}$, in which a graph GR that represents the average diameter of the coronary arteries is displayed; a window $W_{ST\text{-}CPR}$, in which a straight CPR (Curved Planar Reconstruction) image ST-CPR of the coronary arteries is displayed; a window $W_{MPR\text{-}0}$, in which an MPR (Multi Planar Reconstruction) image MPR-0 that represents a orthogonal cross section, windows $W_{MPR\text{-}1}$, $W_{MPR\text{-}2}$, and $W_{MPR\text{-}3}$, in which three MPR images MPR-1, MPR-2, and MPR-3 that respectively represent an axial, sagittal, and coronal cross section are displayed; a window $W_{SCCPR}$, in which a stretch CPR image SC-CPR is displayed, and a window $W_{VR}$, in which a Volume Rendering image VR is displayed. The diagnostic screen having this layout is that which is illustrated in FIG. 2B.

A label that indicates the relationships among images are displayed along with the images in each window. In FIG. 2B, two arrows that point toward each other are displayed within the images in windows $W_{MPR\text{-}1}$, $W_{MPR\text{-}2}$, $W_{MPR\text{-}3}$, $W_{SC\text{-}CPR}$, and $W_{VR}$. These arrows point at the same position within the subject from the same directions. A user can understand the correspondent relationships among cross sections which are displayed as MPR images and a position within the VR image by observing the images while comparing the locations and directions of the arrows.

If one of the image windows within the image region IMG is selected by a clicking operation or the like, the image window is switched to an active state. Thereafter, the display within the image window in the active state is controlled by user operations using the mouse or the like. Meanwhile, the display within the image windows that were not selected is controlled irrelevant to user operations, because the non selected image windows are in an inactive state.

An operation interface including buttons, radio buttons, and the like is arranged within the operating region OP. The operation interface differs according to the target of diagnosis (such as types of organs). However, a layout change button LC and a save button SV are constantly displayed, regardless of the target of diagnosis.

Figure 2C:
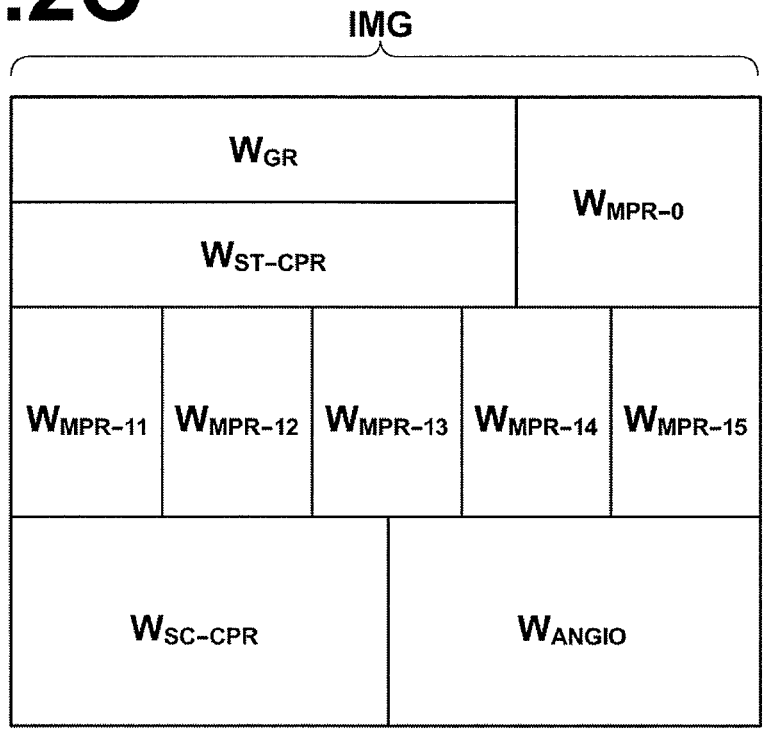
FIG. 2C is a diagram that illustrates a second example of the layout of a diagnosis screen.
Figure 2D:
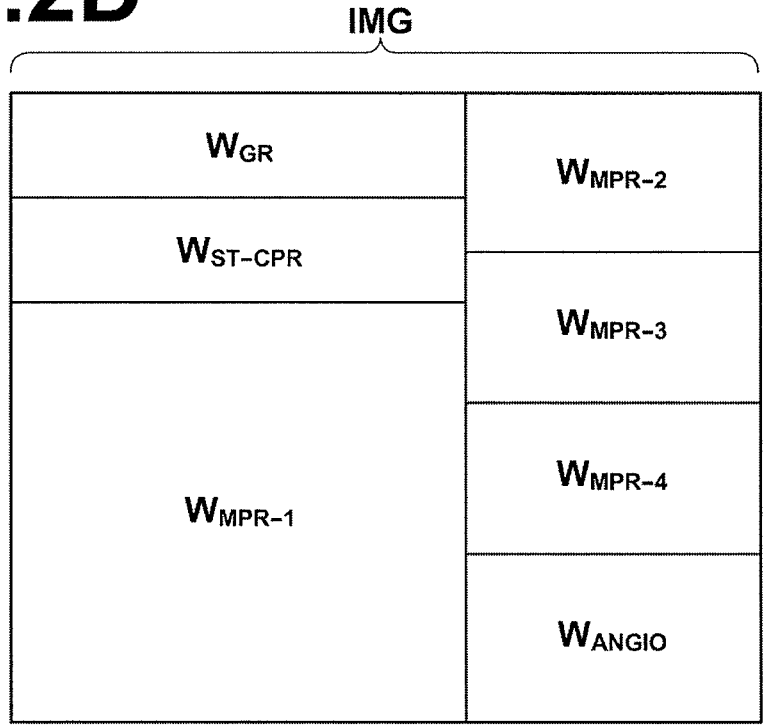
FIG. 2D is a diagram that illustrates a third example of the layout of a diagnosis screen.
Figure 2E:
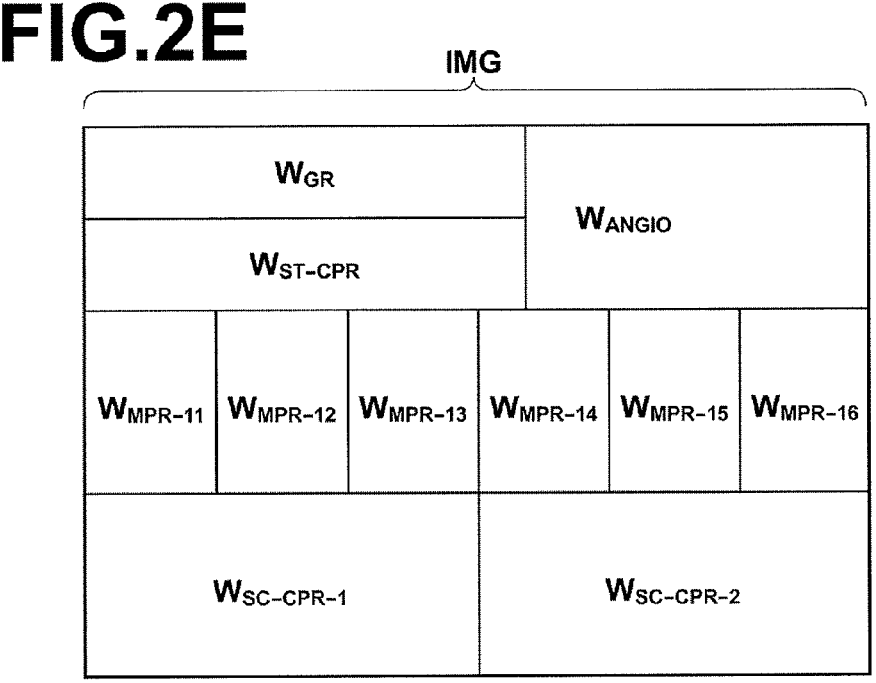
FIG. 2E is a diagram that illustrates a fourth example of the layout of a diagnosis screen.

The layout change button LC is a button that functions as a trigger that causes a user interface for changing the arrangement of each image window within the diagnosis screen (such as the order in which the image windows are arranged, and the shape and size of each image window), and for changing the contents of the images which are displayed (such as generation methods and parameters). For example, if the layout change button LC is clicked within the diagnosis screen, templates that represent arrangements of each image window and the contents of the images displayed therein, such as those illustrated in the image region IMG of FIG. 2A and the image regions IMG of FIGS. 2C through 2E are displayed in a row. When the user selects a desired template from among the displayed templates by a clicking operation, the layout of the image region within the diagnosis screen is changed. Note that in the Figures, $W_{ANGIO}$ is a blood vessel image (angiograph), and $W_{MPR-11}$ through $W_{MPR-16}$ are MPR images that represent orthogonal cross sections of predetermined positions along the coronary arteries.

In addition, if the save button SV is clicked within the diagnosis screen, an image of the screen which is being displayed at that time is saved as a snapshot.

The data which is stored as the snapshot may be image data that represent an image of the entire display screen. In the present embodiment, the group of parameters which were set when the images which are being displayed were generated (for example, the ranges which are displayed as CPR images, the positions and orientations of the cross sections displayed as MPR images, the viewpoint of volume rendering, and the like) are saved as the snapshot. When the saved screen is to be reproduced later, each of the images is generated from the volume data using these parameters again, and then the generated images are displayed. According to this saving method, a saved screen can be reproduced, and thereafter, new images can be displayed by adjusting parameters using the reproduced state as a reference. For example, the orientations of cross sections can be adjusted, and new cross sectional images can be displayed.

Figure 3:
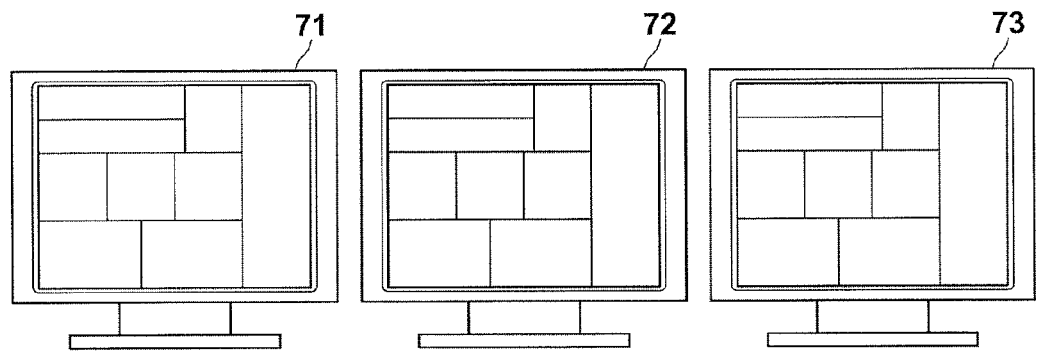
FIG. 3 is a diagram that illustrates a comparative image observation method that utilizes a snapshot function.

Screens which are saved as snapshots can be reproduced at a later time easily by performing predetermined operations, and adjustments are also possible following reproduction. Accordingly, three monitors can be arranged alongside each other as illustrated in FIG. 3, a diagnosis screen 71, in which current images obtained by a most recent examination are arranged, can be displayed on one of the monitors, and diagnosis screens 72 and 73, which are reproduced from snapshots that were saved in the past, can be displayed, and comparative image observation can be performed. However, the number of monitors limits the number of diagnosis screens if this method is employed. In addition, as the number of monitors increases, it becomes difficult for the images to be compared to be within the field of view of a user simultaneously, and frequent movement of line of sight over a wide range will become necessary.

In contrast, the system of the present embodiment adopts a user interface that enables comparative image observation to be performed comfortably even if only one monitor is provided, as will be described below. In the present embodiment, a comparative image observation function is switched ON by settings performed in a setting screen in advance, or by the user performing a predetermined operation while observing images. The user interface when the comparative image observation function is ON will be described with reference to FIG. 4A through FIG. 6.

When an image window is switched to the active state in a state that the comparative image observation function is ON, the window region of the image window is automatically expanded. Specifically, new window regions (temporary display regions) appear about the periphery of a region of the image window which had been being displayed previously, that is, a region which is always displayed regardless of the state of the image window (constant display region).

One or a plurality of thumbnail images, which are the objects of comparative image observation, are displayed within the temporary display regions that newly appear. Assuming that the image for observation which is displayed in the constant display region is an image that represents the state of a subject at a certain point in time, the thumbnail images are images that represent the state of the subject at other points in time, in the same observation format as that of the image for observation. For example, if the image for observation is an MPR image that represents a cross section X of the subject, the thumbnail images are thumbnail MPR images that represent the cross section X of the subject as well.

Figure 4A:
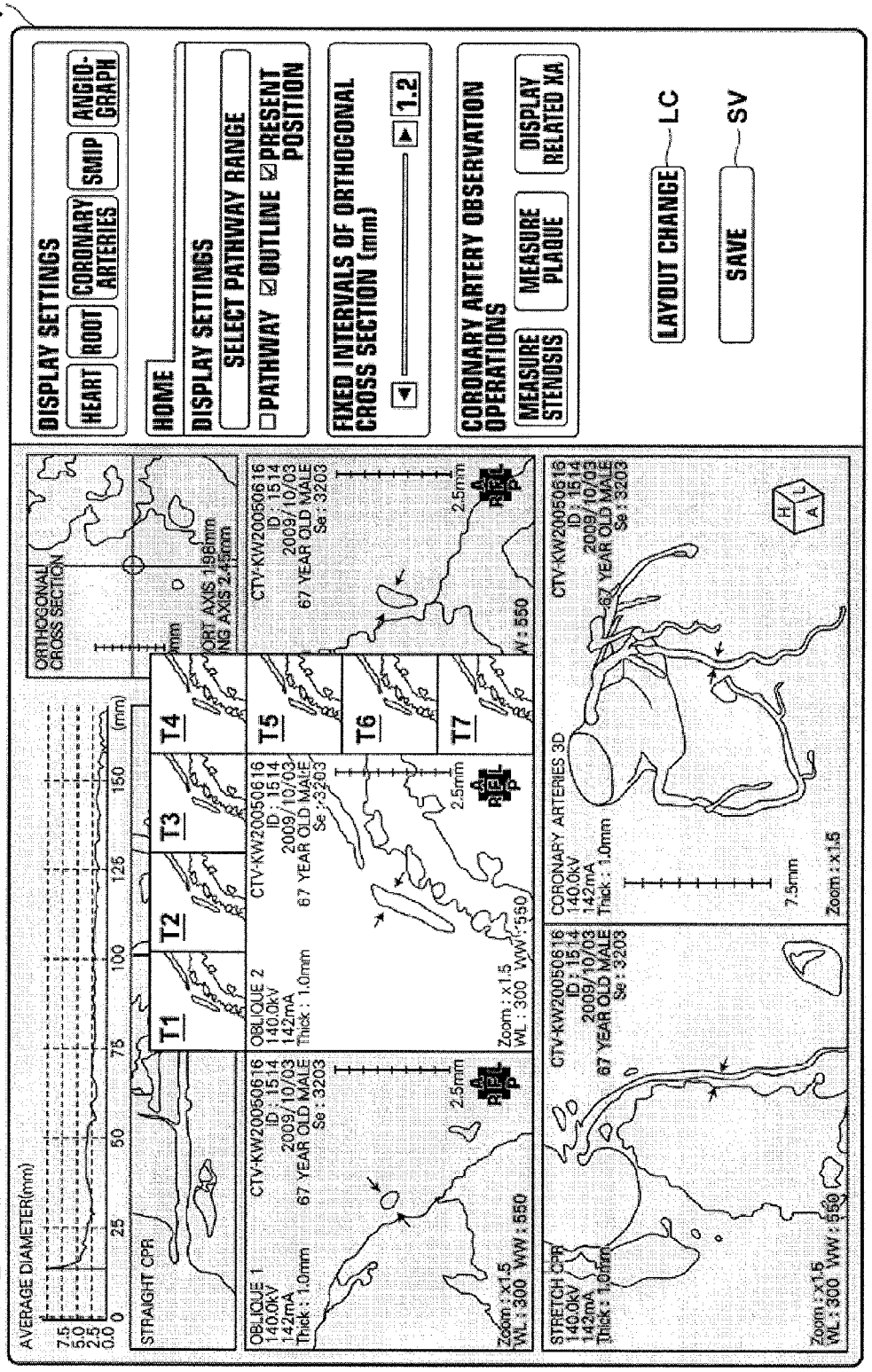
FIG. 4A is a diagram that illustrates an example of a diagnosis screen displayed by the system of the embodiment of the present invention.

For example, FIG. 4A is a diagram that illustrates a screen 74, which is the screen 71 illustrated in FIG. 2A and FIG. 2B when the image window $W_{MPR-2}$ is activated. As illustrated in FIG. 4A, when the image window $W_{MPR-2}$ is switched to the active state temporary display regions appear above and toward the right of the image for observation MOR-2, which is displayed in the image window, so as to surround the image window $W_{MPR-2}$. Thumbnail MPR images T1 through T7 are displayed within the temporary display regions.

Here, the shape of the expanded image window and the positions that the thumbnail images are displayed in varies according to the shape and size of the constant display region, the number of thumbnail images, the contents of the surrounding image windows, and the position of the image window with respect to the screen as a whole.

For example, in the case that a constant display region is long in the horizontal direction, the temporary display regions will appear above or below the constant display region, but not toward the right or the left thereof. If images which are long in the horizontal direction are arranged side by side, the amount of movement of lines of sight during image observation is likely to become great. However, if they are arranged in the vertical direction, the amount of movement of lines of sight can be kept small.

In addition, in the case that an image is displayed within a neighboring inactive image window which is suited to be viewed simultaneously with the image within an active image window, the temporary display regions appear at positions that do not overlap with the neighboring image window.

Figure 4B:
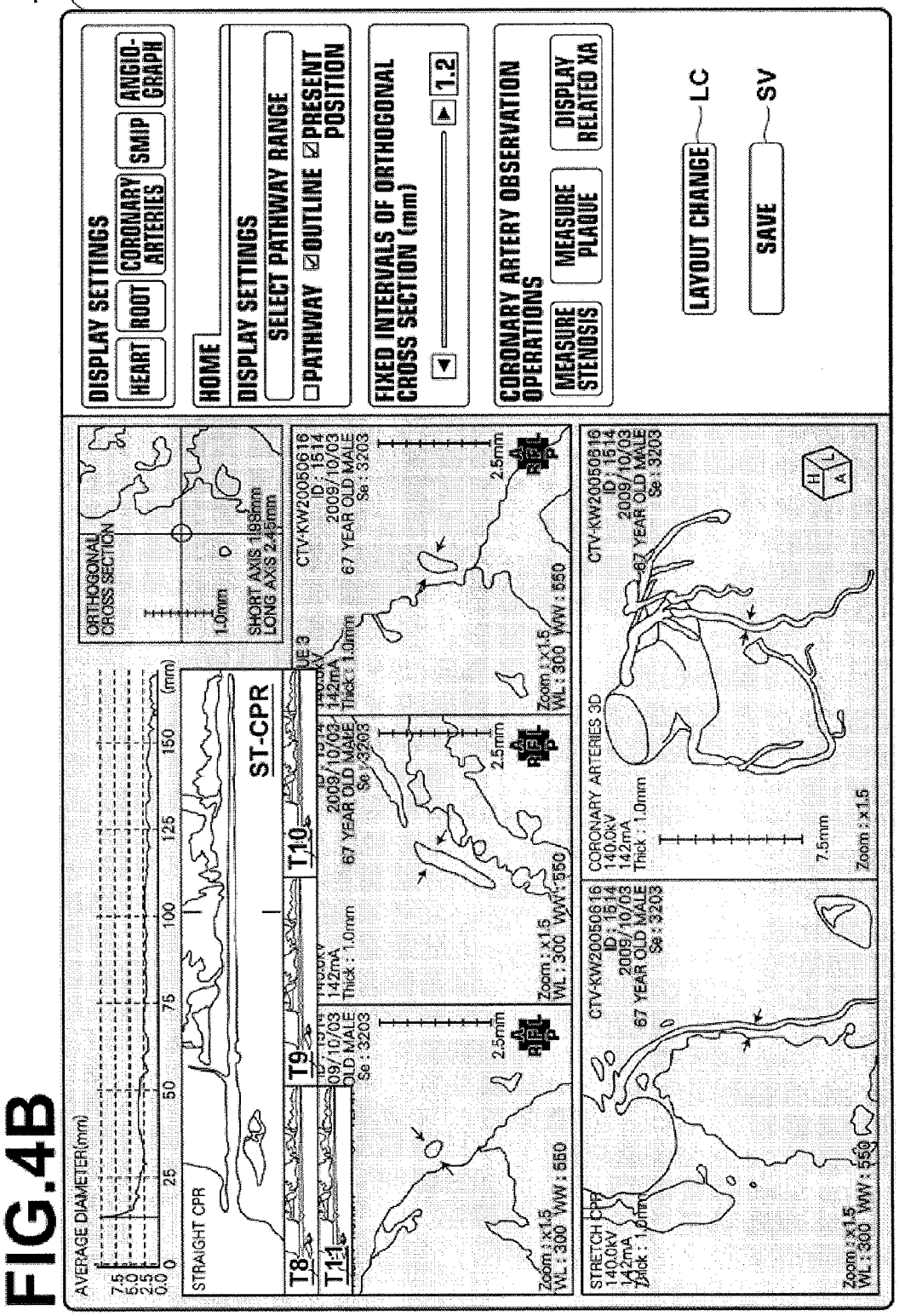
FIG. 4B is a diagram that illustrates another example of a diagnosis screen displayed by the system of the embodiment of the present invention.

For example, FIG. 4B illustrates a screen 75, in which the image window $W_{ST-CPR}$ is switched to the active state. The straight CPR image is long in the horizontal direction, and it is favorable for the straight SPR image to be viewed along with the graph that represents the average diameter. Therefore, thumbnail CPR images T8 through T11 appear only beneath the existing straight CPR image in the screen 75. Note that as illustrated in FIG. 4B, the thumbnail images are not necessarily limited to appearing adjacent to an image which is being displayed, and may be displayed in two rows (or three or more rows).

In the case that an image window is adjacent to the operating region OP, the temporary display regions do not appear within the operating region. This configuration is adopted such that operations to be performed within the operating region OP are not hindered by the image window being expanded. For example, in the case that the image window $W_{VR}$ is switched to the active state, thumbnail VR images T12 through T15 appear only toward the left or above the VR image which is being displayed, as illustrated in FIG. 4C.

Figure 4C:
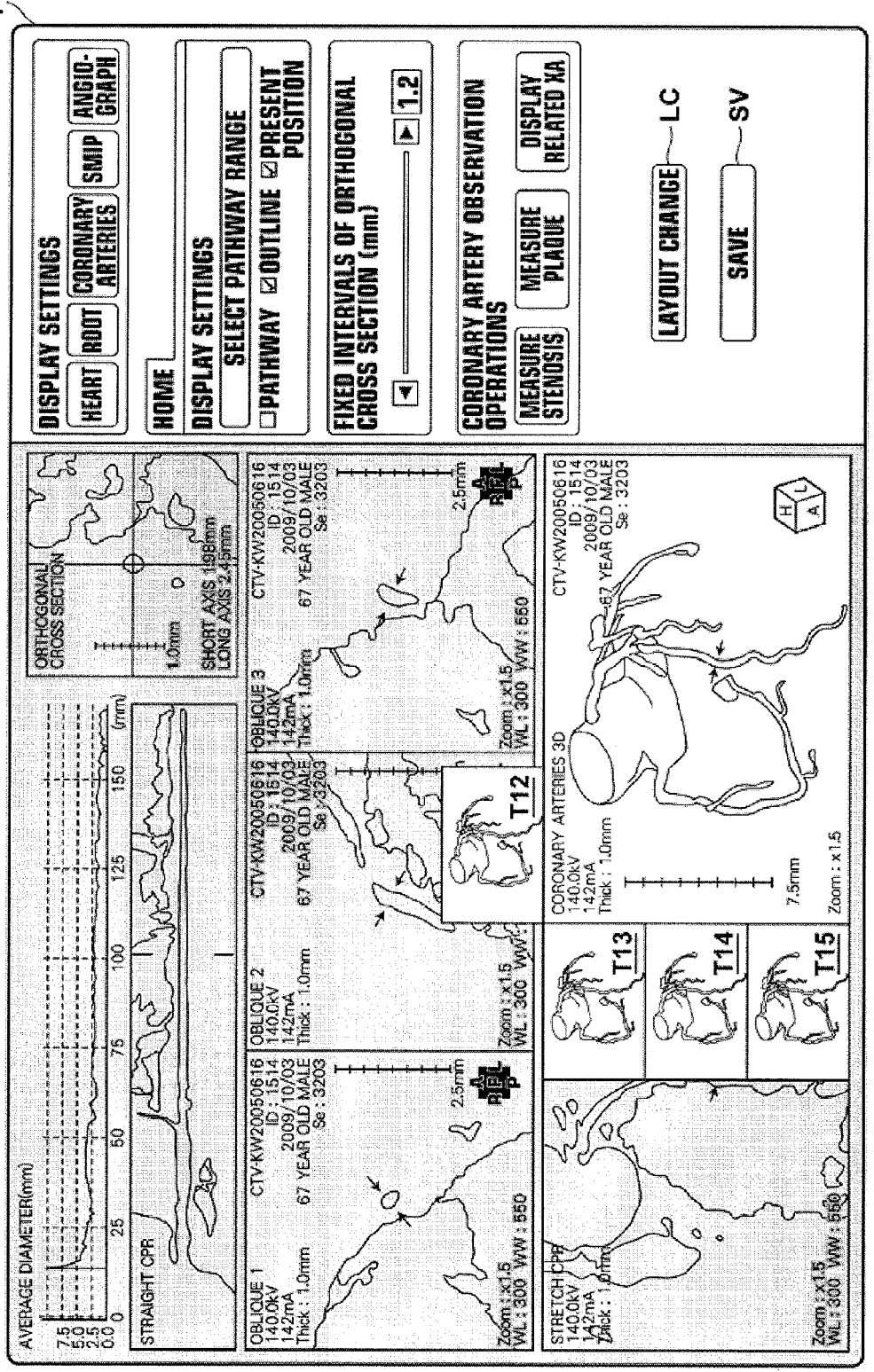
FIG. 4C is a diagram that illustrates yet another example of a diagnosis screen displayed by the system of the embodiment of the present invention.

Note that although not illustrated in FIG. 4A through FIG. 4C, it is preferable for the thumbnail images to be displayed with imaging dates/times appended thereto, in a manner similar to that of the images for observation. By adopting this configuration, the user can easily confirm the imaging dates and times of the image for observation and the thumbnail images during comparative image observation.

Next, operations to be performed with respect to the image window in the active state and the operations of the image window when such operations are performed will be described. In the present embodiment, an image for observation corresponding to a specified thumbnail image within a temporary display region replaces an image for observation within the constant display region, when a thumbnail image within a temporary display region is specified and a first operation is performed. In addition, an image for observation corresponding to a specified thumbnail image replaces the specified thumbnail image, when a thumbnail image within a temporary display region is specified and a second operation is performed. The specific operations of the image window will be described with reference to FIG. 5 and FIG. 6.

Figure 5:
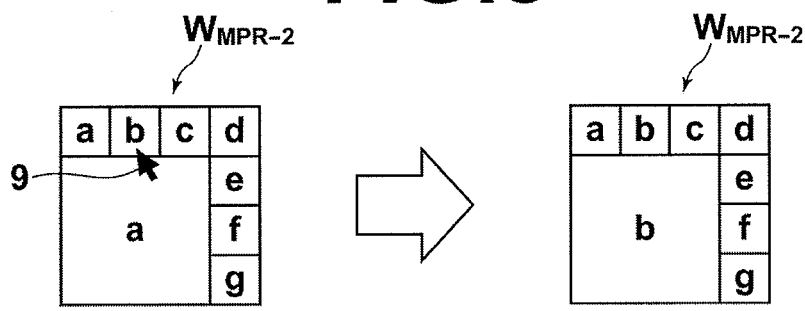
FIG. 5 is a diagram that illustrates an example of the operation of an image window.
Figure 6:
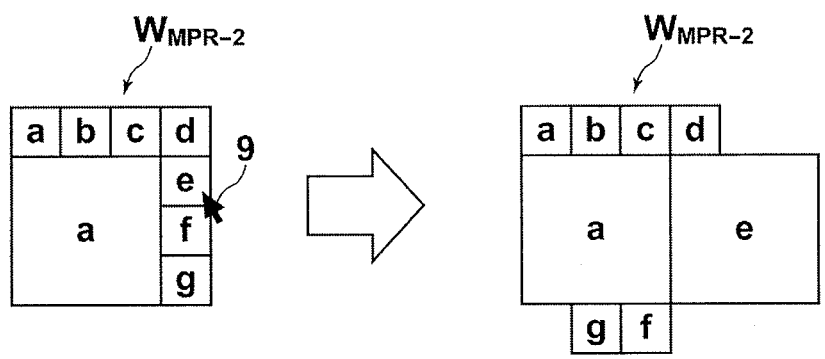
FIG. 6 is a diagram that illustrates another example of the operation of an image window.

In FIG. 5 and FIG. 6, the diagram toward the left illustrates the layout of the image window $W_{MPR-2}$ at a certain point in time, and the diagram toward the right illustrates the layout of the image window $W_{MPR-2}$ after operations are performed during the state illustrated in the leftward diagram. Images a through g are images that represent a subject with the same observation format, but represent the states of the subject on different imaging dates/times (different examination dates, for example). Note that the letters a through g that denote the images are merely labels to differentiate the contents of the images. In the following description, the same letters denote the same images as long as the contents thereof are the same, regardless of the size thereof (regardless of whether the images are images for observation or thumbnail images).

As illustrated in the diagrams toward the left sides of FIG. 5 and FIG. 6, an image for observation a is displayed within the constant display region, and thumbnail images a through g are displayed within the temporary display regions of the image window $W_{MPR-2}$ at a certain point in time. At this time, the thumbnail images a through g within the temporary display regions are displayed in ascending or descending order, based on the imaging dates/times thereof.

When a cursor 9 is positioned on the thumbnail image b and the left mouse button is clicked in the state illustrated in the leftward diagram of FIG. 5, the image for observation a within the constant display region is replaced with an image for observation b corresponding to the thumbnail image b which was specified by the cursor, as illustrated in the rightward diagram of FIG. 5. If the cursor 9 is positioned on another thumbnail image and the same operation is performed, the image for observation b within the constant display region will be replaced by an image for observation corresponding to the thumbnail image. By performing this operation, users can display images which are displayed as thumbnail images at a larger size when they wish to view the images in detail. In other words, by arranging the images as thumbnail images on the screen when detailed observation is not to be performed, the screen of a single monitor can be utilized efficiently.

When the cursor 9 is positioned on the thumbnail image e and the right mouse button is depressed in the state illustrated in the leftward diagram of FIG. 6, the thumbnail image e is replaced by an image for observation e corresponding to the thumbnail image e for the duration of time that the right mouse button is depressed, as illustrated in the rightward diagram of FIG. 6. At this time, the thumbnail images f and g move beneath the constant display region automatically. When the right mouse button is released, the layout of the image window returns to that which is illustrated in the leftward diagram of FIG. 6. If the cursor 9 is positioned on another thumbnail image and the same operation is performed, a similar screen transition will occur. By performing this operation, users can temporarily cause pairs of images that they wish to compare to be arranged alongside each other at the same size, and observe the pairs of images.

By repeating the operations illustrated in FIG. 5 and FIG. 6, users are enabled to cause desired pairs of that they wish to compare to be arranged alongside each other at the same size, and observe the pairs of images.

In addition, in the case that an operation to change the direction of the line of sight (rotation) or an operation to change the range of display (parallel movement/zoom) is performed with respect to the image for observation being displayed in the constant display region of an image window in the active state, the directions of lines of sight and the ranges of display of the thumbnail images which are displayed within the temporary display regions are automatically changed in a coordinated manner along with changes which are administered on the direction of the line of sight and the range of display of the image for observation of the constant display region. Accordingly, the thumbnail images which are displayed about the periphery of the image for observation will always be images having the same observation format as that of the image for observation, without the need to adjust the observation format of each image individually. Note that the updating of the display of the constant display region and the updating of the display of the temporary display regions may be performed in a synchronized manner.

The method by which the user interface described above is realized will be clarified, by describing the processes performed by the image window control means 61, the display control means 62, the image generating means 63, and the client side (C) volume data selecting means 64 of FIG. 1.

Figure 7:
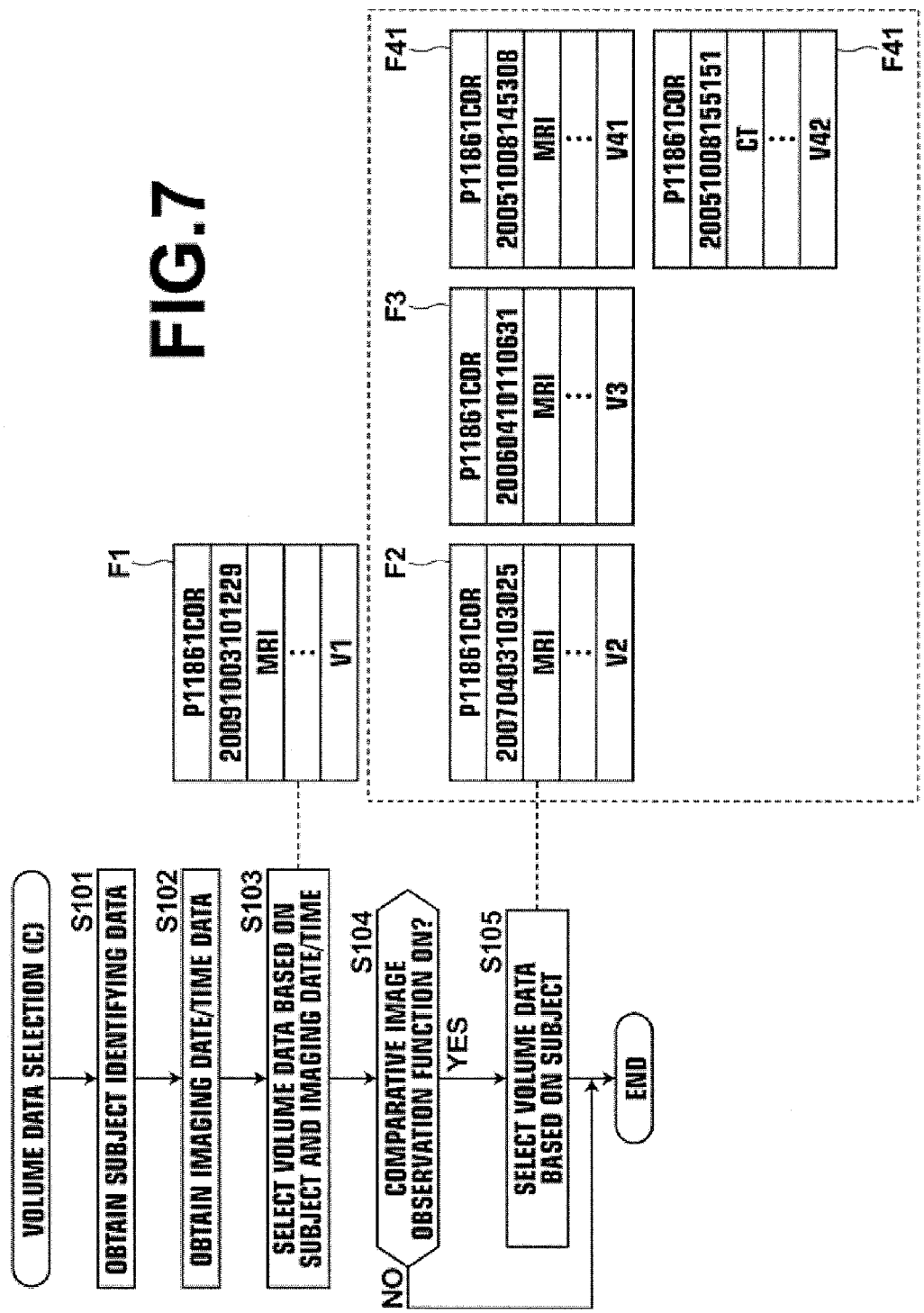
FIG. 7 is a flow chart that illustrates the steps of a process performed by a volume data selecting means (C).

In the present embodiment, first, necessary data is input in an initial screen, then a data selecting process is executed by the volume data selecting means 64. FIG. 7 is a flow chart that illustrates the steps of the process performed by the volume data selecting means 64.

The volume data selecting means 64 causes the aforementioned initial screen and the dialog box to be displayed. Then, the subject identifying data and the imaging date/time data are obtained, by detecting a function selecting operation or an operation that specifies a patient and imaging date/time performed by a user (steps S101, S102). At this time, in the case that a reference period is specified within the aforementioned dialog box, data for the reference period are also obtained.

In the present embodiment, the subject identifying data are combinations of patient ID numbers and symbols that represent bodily portions which are targets of diagnosis. For example, in the case that the ID number of a patient is P11861 and the bodily portion is the coronary arteries represented by symbols COR, the subject identifying data is P11861COR.

The patient ID number is input or selected at the initial screen. In addition, the diagnosis assisting functions provided by the present embodiment differ according to the bodily portion which is the target of diagnosis (organs, bones, muscles, blood vessels, etc.). Therefore, the bodily portion which is to be the target of diagnosis is determined by the user selecting a diagnosis assisting function. Accordingly, the subject identifying data can be obtained, by detecting the function selecting operation and an operation that specifies a patient.

In the present embodiment, the imaging date/time data is a 14 digit numerical value that represents the imaging date (year in AD, month, and day) and the imaging time (hour, minute, and second). This numerical value is input or selected by the user in the aforementioned dialog box. The reference period is specified by an eight digit numerical value that represents a starting point and an endpoint of the reference period. Alternatively, the reference period may be specified by a one to two digit numerical value that represents a number of years or a number of months. Note that the imaging date/time specified by a user may only be a portion of the imaging date and time, for example, only the year, month, and day.

Next, the volume data selecting means 64 selects volume data to be employed to generate images for observation, based on the subject identifying data and the imaging date/time data (step S103). Specifically, the subject identifying data and the imaging date/time data are sent to the volume data selecting means 42 of the data server 4, and a search is requested among the files stored in the high capacity storage 5.

The volume data selecting means 42 selects files to which subject identifying data and imaging date/time data having the same values as the subject identifying data and the imaging time/date data received from the volume data selecting means 64, from among the files which are stored in the high capacity storage 5. The volume data selecting means 42 sends the selected files to the volume data selecting means 64. FIG. 7 illustrates an example in which a file having subject identifying data of P11861COR, imaging date/time data of 20091003101229 (10:12:29, Oct. 3, 2009), and modality data that represents an imaging modality of MRI is selected. Note that with respect to the imaging date/time data, files of which the imaging times/dates partially match the received imaging time/date data, such as matches among only the imaging year, month, and date, may be selected.

Thereafter, the volume data selecting means 64 judges whether the comparative image observation function is ON (step S104). Whether the comparative image observation function is ON may be judged by referring to setting flags stored in the memory for each function (flags that take a value of 1 when the function is ON, and take a value of 0 when the function is OFF), for example.

In the case that the comparative image reading function is ON, the volume data selecting means 64 again selects volume data sets to be employed to generate images for observation, based on the subject identifying data (step S105). The sets of volume data are selected by requesting that the volume data selecting means 42 search for files that include pertinent volume data, in a manner similar to that employed in step S103. However, in step S105, the imaging date/time data is not sent when requesting the search. Thereby, a plurality of sets of volume data regarding the specified subject and obtained on different imaging dates and times are selected.

FIG. 7 illustrates an example in which files F2, F3, F41, and F42, having 20070403103025, 20060410110631, 20051008145308, and 20051008155151 appended respectively thereto as imaging date/time data are selected. As illustrated by the fact that files F41 and F42 are selected, there are cases that two (or three or more) files of which the subject identifying data and the imaging date match those of the search request and have different modalities are selected. An example of such a case in that in which an MR apparatus is employed for periodic physical examinations, and a CT apparatus is employed for a detailed follow up examination. Another possible case is that in which a plurality of sets of volume data are obtained at a plurality of points in time accompanying ingestion of imaging agents. In this case, a two or more files having the same imaging date as the search request and a common imaging modality and different times within the imaging date/time data may be selected. In addition, there may be cases in which sets of volume data having a common imaging modality but different imaging methods or different imaging conditions are selected.

Note that if a reference period is specified in the aforementioned dialog box, the volume data selecting means 64 also sends imaging date/time data that represent the starting point and the endpoint of the reference period (reference period date/time data) to the volume data selecting means 42. Here, in the case that the reference period is represented by a number of years or a number of months, such as "the past two years" and "the past six months", the starting point and the endpoint of the reference period are determined based on the current date. The determined starting point and endpoint of the reference period are converted into imaging date/time data, and sent to the volume data selecting means 42.

Meanwhile, in the case that the comparative image observation function is OFF, the process of step S105 is not executed.

Figure 8:
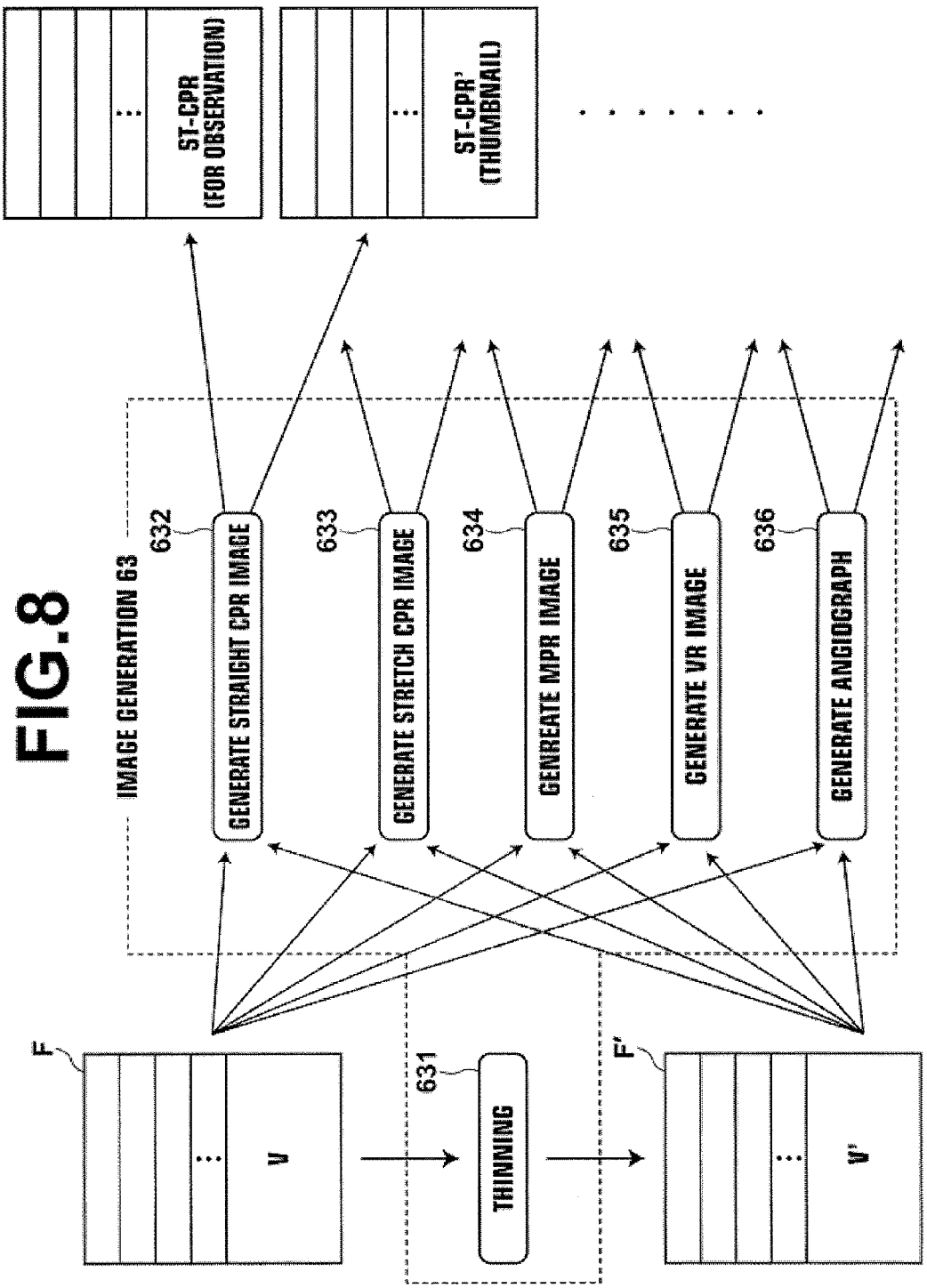
FIG. 8 is a diagram that illustrates the schematic structure of an image generating means and a process performed thereby.

Next, the structure of the image generating means 63 and the processes performed thereby will be described. As illustrated in FIG. 8, in the present embodiment, the image generating means 63 is equipped with: a managing section (not shown) that manages the entirety of the image generating processes; a thinning section 631; a straight CPR image generating section 632; a stretch CPR image generating section 633; an MPR image generating section 634; and a VR image generating section 635. In other words, the programs that define the processes which are executed by the image generating means 63 include: a main program; and a plurality of program module groups that respectively define a thinning process, a straight CPR image generating process, a stretch CPR image generating process, an MPR image generating process, and a VR image generating process.

Figure 9:
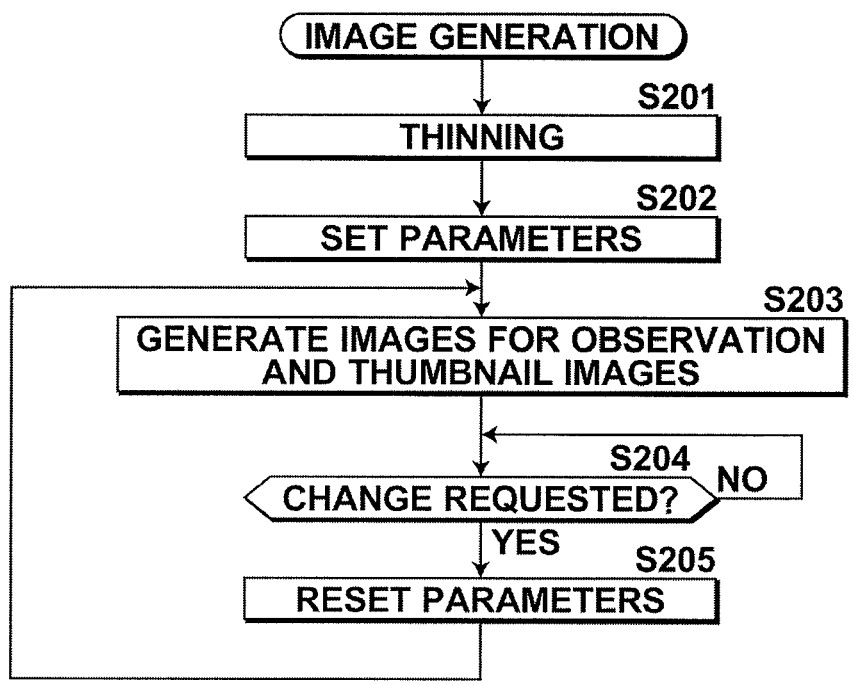
FIG. 9 is a flow chart that illustrates the steps of a process performed by the image generating means.

Note that methods for generating CPR images, MPR images, and the like are known, and therefore, a detailed description of the processes which are executed by each of the sections that constitute the image generating means will be omitted. The flow of processes performed by the image generating means will be described as a whole, with reference to FIG. 8 and FIG. 9.

When the files F selected by the volume data selecting means 64 are supplied to the image generating means 63, first, the thinning is executed by the thinning section 631 (step S201). The thinning section 631 extracts sets of volume data V excluding header data from the files F, and generates sets of volume data V', which are of smaller data sizes than the sets of volume data V.

The sets of volume data V are thinned such that the data size of the sets of volume data V' is approximately ⅛ that of the sets of volume data V, for example. The thinning section 631 stores the sets of volume data V' in the memory as files F'. At this time, data recorded in the header regions of the files F are copied into the header regions of the files F', and further, information that indicates that the files F' are thinned data files is also written into the header regions.

Note that the files F that include the sets of volume data V are saved in the memory without being updated after the sets of volume data V' are generated.

Next, the image generating means 63 sets initial parameters to be supplied to the image generating sections 632 through 635 (step S202). The parameters necessary for the processes of the image generating sections 632 through 635 differ for each image generating section, that is, for each observation format of the images to be generated. For example, it is necessary to supply parameters that specify ranges of display in the path directions of the coronary arteries to the straight CPR image generating section 632 and the stretch CPR image generating section. In addition, it is necessary to supply parameters that specify the positions and orientations of cross sections to the MPR image generating section 634. Further, it is necessary to supply parameters that specify the position of a viewpoint and the like to the VR image generating section 635. In step S202, the initial values of the parameters to be supplied to the image generating sections 632 through 635 are default values stored in the memory in advance, or values which are set in advance by the user.

Note that in the case that a plurality of images of the same type are to be displayed on the diagnosis screen, a plurality of values are set for a single type of parameter. For example, if MPR images are to be displayed for each of an orthogonal cross section, an axial cross section, a sagittal cross section, and a coronal cross section, four sets of values are supplied to the MPR image generating section 634 as parameters that specify the cross sections.

The image generating sections 632 through 635 generate images for observation and thumbnail images from the sets of volume data V, the sets of volume data V', and parameter values supplied thereto (step S203). For example, the straight CPR image generating section 632 generates straight CPR images for observation using the sets of volume data V and the input parameters, and generates thumbnail straight CPR images using the sets of volume data V' and the input parameters.

AT this time, images for observation ST-CPR and thumbnail images ST-CPR' are generated utilizing the same parameters. Therefore, the observation formats (range of display and the like) are the same, although the sizes thereof are different. The other image generating sections 633 through 635 respectively generate pairs of images of different sizes.

The image generating sections 632 through 635 save the generated images for observation and the generated thumbnail images within the memory or the like as files in a predetermined format. Here, data recorded in the header regions of the files F and the files F' which were utilized to generate the generated images are copied into the header regions of the saved files. Thereby, information regarding the subject, the imaging date/time, the modality, etc. are appended to the generated images for observation and the generated thumbnail images. The image generating sections 632 through 635 further record information that indicates the observation format of the image (image type, parameters, etc.) and whether the image is an image for observation or a thumbnail image (a flag or the like) in the header regions of the files.

The generated images are selectively output to the screen by the display control means 62 and the image window control means 61 as will be described later. Thereby, a diagnosis screen such as that exemplified in FIG. 2B appears on the screen of a display.

If the user performs an operation that requests that the observation format of an image for observation displayed in an image window in the active state in the diagnosis screen, the operation is detected by the image window control means 61 and the display control means 62, then transmitted to the image generating means 63. For example, if the user performs an operation to change the direction of the line of sight in a volume rendering image (an image rotating operation), the display control means supplies data regarding the viewpoint and the line of sight direction specified by the user to the image generating means 63.

When the image generating means 63 receives the request to change the observation format (step S204), it resets the parameters which were set in step S202 according to the user operation (step S205). Each of the image generating sections 632 through 635 generates images for observation and thumbnail images again, based on the sets of volume data V, the sets of volume data V', and the parameter values which were reset in step S205.

The images for observation and the thumbnail images generated by the image generating means 63 according to the operations performed by the user are output to the screen by the display control means 62 and the image window control means 61. Thereby, the display of the image window in the active state is updated. For example, in the above example, the subjects, such as the coronary arteries, displayed in the volume rendering image for observation and the thumbnail volume rendering image, each rotate. At this time, by matching the timings at which the display of each image is updated, the subject within the images can be synchronously rotated.

Figure 10:
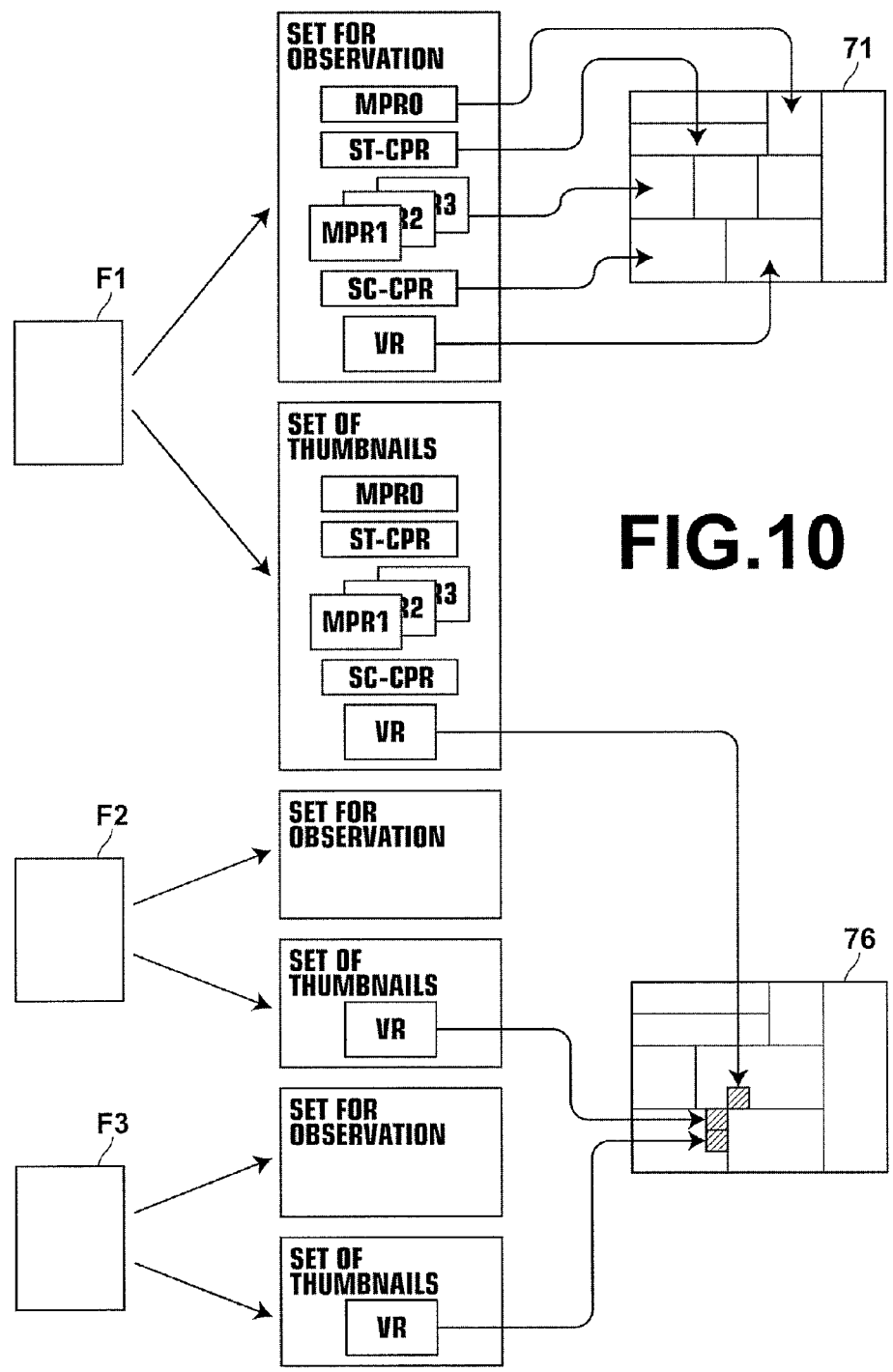
FIG. 10 is a diagram that illustrates the relationship between the process performed by the image generating means and a process performed by a display control means.

FIG. 10 is a diagram that illustrates the relationship between the process performed by the image generating means 63 and a process performed by a display control means 62. Here, an example will be described in which the layout of the image window is that illustrated in FIG. 2A, FIG. 2B, and FIG. 4C. As illustrated in FIG. 10, N files (for example, three files F1 through F3) are selected by the volume data selecting means 64. In this case, the image generating means 63 generates N sets of images for observation that includes a plurality of types of images for observation to be displayed in each image window, and N sets of thumbnail images corresponding to the sets of images for observation. As described previously, information regarding the subject, the imaging date/time, the modality, the observation format (image type, parameters, etc.) and whether the image is an image for observation or a thumbnail image is added to the images for observation and the thumbnail images as header data.

The display control means 62 checks the imaging date/time data included in the header data of each image for observation within the N sets of images for observation against the imaging date and time input or selected by the user, and selects one set of images for observation of which the imaging date and time match. Here, in the case that the imaging date and time input or selected by the user is a portion of the imaging date and time, such as only the year, month, and day, the set of images for observation is selected by a partial match. FIG. 10 illustrates a case in which a set of images for observation generated from volume data included in the file F1 is selected. The display control means 62 outputs each of the images for observation included in the selected set of images for observation to the corresponding constant display region of the image window. Thereby, the diagnosis screen 71 illustrated in FIG. 2B is displayed.

The display control means 62 further refers to the data regarding observation format, included in the header data of each thumbnail image within the N sets of thumbnail images. The display control means 62 checks the referred data against the data regarding the observation format, appended to the images for observation which are displayed in an image window in an active state (here, image window $W_{VR}$), and selects thumbnail images having matching observation formats. Then, the selected thumbnail images are sorted in descending or ascending order of imaging dates/times, based on the imaging time/date data included in the header data, and output to the temporary display regions of the active image window. FIG. 10 illustrates an example in which thumbnail volume rendering images are selected from each of three sets of thumbnail images generated from the files F1 through F3. The display control means 62 outputs the three selected thumbnail volume rendering images to the window $W_{VR}$ in the active state, as illustrated in FIG. 10. Thereby, the diagnosis screen 76 illustrated in FIG. 4C is displayed.

Figure 11:
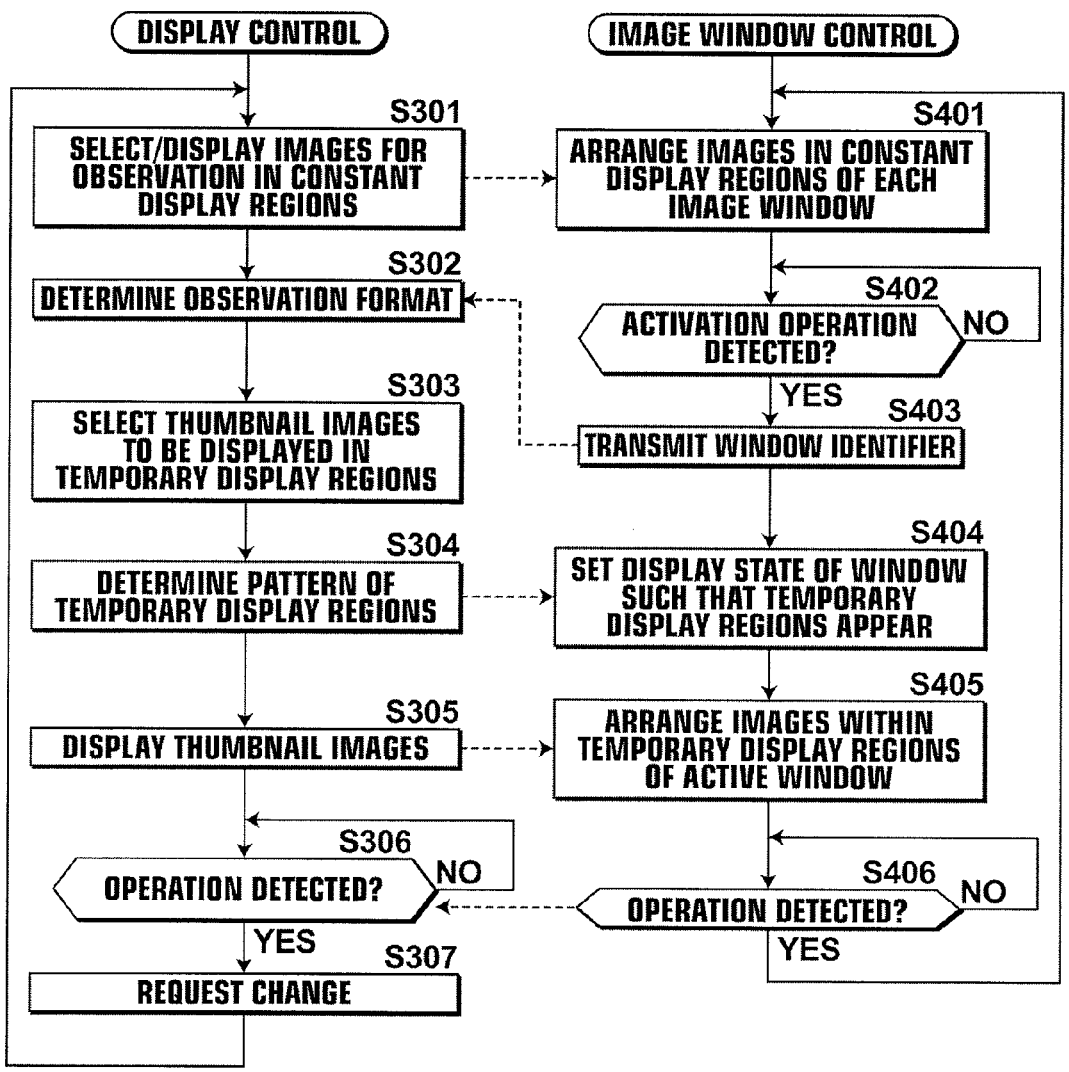
FIG. 11 is a flow chart that illustrates the steps of a process performed by the display control means and the steps of a process performed by an image window control means, correlated with each other.

FIG. 11 is a flow chart that illustrates the steps of a process performed by the display control means 62 and the steps of a process performed by an image window control means 61, correlated with each other. When a set of images for observation to be displayed in the constant display regions is selected, the display control means 62 requests the image window control means 61 to display the images for observation to be displayed in the constant display region of each image window (step S301). Which image for observation is to be displayed in which image window is specified by window identifiers (handles or the like). The image window control means 61 that receives the aforementioned request arranges images in the constant display regions of each image window, to form a diagnosis screen such as that illustrated in FIG. 2B (step S401).

When the user performs an operation to activate one of the image windows, the operation is detected by the image window control means 61 (step S402), and the display control means 62 is notified of the identifier of the activated window (step S403). The display control means 62 determines the observation format of the image for observation which is displayed in the activated image window based on the identifier of the activated window (step S302). Then, the display control means 62 selects thumbnail images having the same observation format as that of the image for observation to be displayed in the temporary display regions of the activated window (step S303).

Next, the display control means 62 determines the pattern of the temporary display regions, based on the observation format of the images displayed in the activated image window and the number of selected thumbnail images (step S304). One or more of the upward, the leftward, the downward, and the rightward directions with respect to the constant display region is selected as the direction or directions in which the temporary display regions expand. The temporary display regions may be form a single continuous region as exemplified in FIG. 4A and FIG. 4B, or may form a plurality of regions that expand in different directions as exemplified in FIG. 4C.

As described previously with reference to FIG. 4A through FIG. 4C, the preferred shape of the temporary display regions differs according to the position of the image window with respect to the screen as a whole, and the type of image the image for observation is. In addition, whether expansion in a single direction is sufficient, or expansion in a plurality of directions is necessary also depends on the shapes and number of the selected thumbnail images. For this reason, in the present embodiment, correspondent relationships among patterns of the temporary display regions with the positions of the image windows, the observation formats, and the number of thumbnail images are defined in advance. In step S304, the pattern of the temporary display regions is determined by referring to the definition data. The image window control means 61 sets the display state of the image window such that the temporary display regions of the pattern determined by the display control means 62 appears on the screen (step S404).

The display control means 62 sorts the selected thumbnail images in descending or ascending order of imaging dates/times, based on the imaging time/date data included in the header data thereof, parallel to the process of step S404. The display control means 62 supplies the image window control means 61 with the sorted thumbnail images, and requests display thereof within the temporary display regions (step S305). When this request is received, the image window control means 61 arranges the thumbnail images in the temporary display regions (step S405). At this time, which position is designated as the starting point of the image arrangement is defined in advance, and recorded as definition data. In step S405, the thumbnail images are arranged based on the definition data.

If the user performs an operation to change the observation format, for example, an operation to change the direction of line of sight (rotation) or an operation to change the range of display (movement/change in size), the operation is detected by the image window control means 61 (step S406), and transmitted to the display control means 62 (step S306). When the user operation is detected, the display control means 62 supplies parameters that indicate the line of sight or the range of display specified by the user, and requests a change in the observation format (step S307). Thereby, the process for generating the images for observation and the thumbnail images is executed again as described previously with reference to FIG. 9, and the display of the diagnosis screen is updated.

Figure 12:
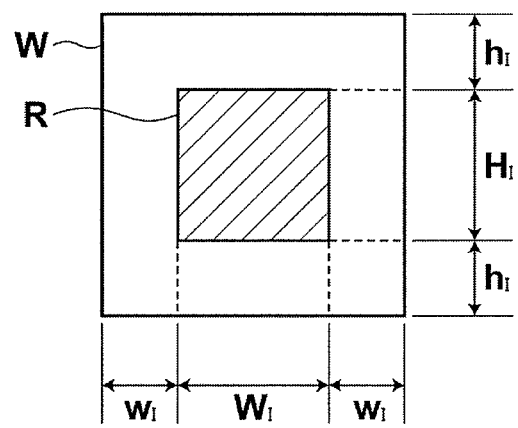
FIG. 12 is a diagram that illustrates the relationship between an image window and a region (in an inactive state).
Figure 13:
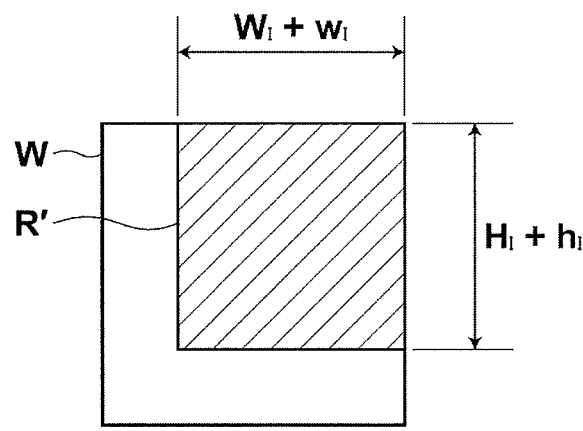
FIG. 13 is a diagram that illustrates the relationship between an image window and a region (in an active state).

Here, the temporary display regions will be described further with reference to FIG. 12 and FIG. 13. In the Windows™ platform, it is possible to change the visually perceived shape of an image window W, by setting a region R within the image window W and resetting the shape of the region R. The shape of the region may be set to be a rectangle, an oval, or a polygon. Accordingly, the region R can be set such that the constant display region is within the range of the region R and the temporary display regions are outside the range of the region R when an image window is in the inactive state, and such that both the constant display region and the temporary display regions are included within the range of the region R only when the image window is activated. By adopting these settings, it would be visually perceived by users that the temporary display regions appear only when the image window is activated.

For example, assume a case that an image for observation which is displayed within the constant display region of an image window has a width $W_I$ and a height $H_I$, and thumbnail images to be displayed in the temporary display region have widths $w_I$ and heights $h_I$. In this case, the width $W_W$ and the height $H_W$ of the image window are set to $W_W=W_I+2W_I$ and $H_W=H_I+2H_I$. In the inactive state, a region at the center of the image window having a width of $W_I$ and a height of $H_I$ is set as the region R, and the image for observation is arranged within the region R, as illustrated in FIG. 12. When the image window is activated, a region R', which is the region R expanded by $w_I$ in the rightward direction and by $h_I$ in the upward direction, is set and the thumbnail images are arranged within the expanded region, as illustrated in FIG. 13. Thereby, the diagnosis image 71 illustrated in FIG. 2B can be caused to transition to the diagnosis image 74 illustrated in FIG. 4A.

As described above, past images that users desire to compare against current images appear simply by activating an image window, in which a current image that users desire to compare against past images is displayed, in a diagnosis screen that displays current images in the system of the present embodiment. That is, accumulated past images can be called up for display on the screen by a simple operation such as a single mouse click, without searching for or specifying past images to be compared.

The past images are not displayed in inactive image windows. Therefore, comparative image observation can be performed without confusion even if a great number of images having different observation formats, such as VR images, MPR images, CPR images, and MIP images are displayed on the screen, by sequentially activating each image window.

Because the past images are displayed as thumbnails, comparative image observation can be performed with a great number (10 or greater) of images, even in the case that only a single display is provided. Displaying the past images as thumbnails reduces the screen space occupied by the past images. Therefore, users are enabled to perform comparative image observation without moving their lines of sight greatly. In addition, all of the images which are targets for comparison are displayed on the screen simultaneously. Therefore, the inconvenience of having to perform comparative image observation while retaining one of the images in a user's memory is eliminated. By adopting this configuration, the physical/mental fatigue of users is greatly reduced compared to that caused by conventional systems.

If a thumbnail image is specified and a predetermined operation is performed, the past image which is displayed as a thumbnail is displayed at a size suited for observation. Therefore, there is no possibility that displaying them as thumbnails will impede observation of individual images.

In the case that only images obtained during a certain period prior to and following discovery of an abnormality, it is possible to limit the reference period, thereby limiting the number of past images which are displayed. This configuration enables efficient diagnosis by narrowing the targets of comparison, in cases that a great number of images obtained during periodic physical examinations representing healthy states are stored.

The images for observation and the thumbnail images are both updated in response to user operations to change observation formats. Therefore, the observation formats of an image for observation and thumbnail images within an image window in the active state can be matched. At this time, the updating of the two types of images may be synchronized. In this case, the observation formats of the two types of images will always be matched. This configuration enables users to initiate comparative image observation from a different viewpoint when they desire to compare images from a different viewpoint, simply by performing an operation to change the observation format of an image for observation within an image window in the active state.

In the present embodiment, the thumbnail images are displayed without changing the size of the images for observation from the size that they are displayed within image windows in the inactive state, and also without obscuring portions of the images for observation. Therefore, the images for observation do not become difficult to view due to the image windows becoming activated.

Note that in the above description, an example was described, in which a single set of volume data is selected for each imaging date. However, as exemplified in FIG. 7, there are cases in which imaging operations using different modalities are performed on the same imaging date. In the case that the volume data selecting means 64 selects a plurality of files having the same imaging date data, thinned sets of volume data and images for observation are generated for each of the selected files.

For example, in the case that the files F41 and F42 illustrated in FIG. 7 are selected, a set of thinned volume data V41' is generated from a set of volume data V41 recorded in the file F41, and a set of thinned volume data V42' is generated from a set of volume data V42 recorded in the file F42. Then, the four sets of volume data V41, V41', V42, and V42' are input to the image generating sections of the image generating means 63. At this time, it is not necessary for the image generating section into which the sets of volume data V41 and V41' are input and the image generating section into which the sets of volume data V42 and V42' are input to be the same. Note that in cases that images for observation are generated from a plurality of sets of volume data, the types and number of generated images for observation become greater than those in cases that images for observation are generated from a single set of volume data. In such cases, it is preferable for the displayed images to be switched in response to operations to switch the observation format, if it is difficult to display all of the generated images for observation on a single screen. Alternatively, users may input or select imaging times in addition to imaging dates. In this case, the volume data selecting means 64 is enabled to select a single set of volume data based on the imaging date and the imaging time, and the display control means 62 is enabled to cause images for observation generated from a single set of volume data to be displayed.

Next, modifications to the above embodiments will be described.

In the above embodiment, the volume data selecting means 42 and 64 narrow down sets of volume data which are targets of selection to those within a specified reference period, in the case that the comparative image observation function is ON. Other narrowing conditions may also be employed.

For example, the volume data storage means 41 may have recorded therein files 10, in which examination ID's that identify individual examinations are recorded in the header regions thereof. In this case, the aforementioned dialog box enables users to specify a number of recent examinations for which sets of volume data are to be selected instead of or in addition to specifying the reference period. In this configuration, the volume data selecting means 64 sends a value that represents the specified number of examinations to the volume data selecting means 42. The volume data selecting means 42 then obtains sets of volume data correlated with the specified subject identifying data, sorts them in order of examination dates (imaging dates/times), specifies sets of volume data which were obtained by the specified number of examinations sequentially from the most recent, and sends the sets of volume data to the volume data selecting means 64.

Alternatively, the diagnosis assisting system 1 of the present embodiment may be configured to work in conjunction with a management system for managing image observation reports of medical images or with a management system for managing electronic medical charts. If this configuration is adopted, narrowing the sets of volume data to be targets of selection employing opinion data in the image observation reports and confirmed diagnosis data in the electronic medical charts may be considered. For example, image ID's that identify images are recorded in the header regions of each file in the volume data storage means 41 of the diagnosis assisting system, and opinion data, subject identifying data, and image ID's are correlated with each other and recorded in the image observation report management system. In this case, the aforementioned dialog box of the diagnosis assisting system 1 enables specification of an image observation opinion instead of or in addition to the reference period. Specifically, the user interface may be configured so as to enable selection of whether an abnormality is present, and the type of pattern which is pictured in an image. The volume data selecting means 64 may be configured to access the image observation report management system, obtain image ID's correlated with the specified subject identifying data and the image observation opinion data, and transmit the obtained image ID's to the volume data selecting means 42. In this case, the volume data selecting means 42 obtains sets of volume data correlated with the transmitted image ID's, and transmits the obtained sets of volume data to the volume data selecting means 64. Note that in a similar configuration may be adopted in the case that the diagnosis assisting system 1 is configured to work in conjunction with the electronic medical chart management system. That is, confirmed diagnosis data from the electronic medical charts, subject identifying data, and image ID's may be correlated with each other and recorded in the electronic medical chart management system. As an alternative, the sets of volume data may be correlated with data that identifies opinion data or confirmed diagnosis data corresponding thereto. As a further alternative, the contents of the opinions and the confirmed diagnoses themselves may be recorded in the header regions of the files 10.

If the volume data to be selected are narrowed by various narrowing conditions during selection of volume data in this manner, sets of volume data that do not satisfy the narrowing conditions will not be selected from among sets of volume data correlated with specified subject identifying data. Images for observation and thumbnail images are not generated for sets of volume data which are not selected. Therefore, the display control means 62 is enabled to display only images for which comparative image observation is desired. In addition, because images other than those for which comparative image observation is desired are not generated, the processing load on the system is reduced, and the processing efficiency is improved.

An embodiment in which the display control means 62 performs a narrowing process with respect to thumbnail images to be displayed instead of the volume data selecting means 64 and 42 may also be considered. In this embodiment, specifically, the display control means 62 obtains the reference period which is set in the dialog box instead of the volume data selecting means 64. The display control means 62 then checks the observation format data appended to an image for observation which is being displayed in an image window in the active state. Next, the display control means 62 selects thumbnail images having matching observation formats, ultimately selects only thumbnail images having imaging dates and times within the range of the reference period, and outputs the ultimately selected thumbnail images to the temporary display regions of the image window.

Alternatively, a configuration may be adopted, wherein the number of recent examinations is capable of being specified in the aforementioned dialog box, and the image generating means 63 appends the examination ID's correlated to the sets of volume data to the images for observation and the thumbnail images. In this case as well, the display control means 62 ultimately selects only thumbnail images within the range of the number of recent examinations, in a manner similar to the volume data selecting means 42 described above.

As a further alternative, in a configuration in which the diagnosis assisting system 1 of the present embodiment and the management system for managing image observation reports of medical images or the management system for managing electronic medical charts work in conjunction, the aforementioned dialog box may enable specification of an image observation opinion or a confirmed diagnosis. In this case, the image generating means 63 appends the aforementioned image ID's, which are correlated to the sets of volume data, to the images for observation and the thumbnail images. Then, the display control means 62 accesses the image observation report management system or the electronic medical chart management system to specify the image ID's of thumbnail images to be displayed in a manner similar to the aforementioned volume data selecting means 64, and ultimately selects thumbnail images having the specified image ID's.

If the thumbnail images to be displayed are narrowed by various narrowing conditions during selection of thumbnail images in this manner, thumbnail images that do not satisfy the narrowing conditions will not be selected from among the thumbnail images having the same observation format. Therefore, the display control means 62 is enabled to display only images for which comparative image observation is desired. In this case, images for observation and thumbnail images are generated for sets of volume data that do not satisfy the narrowing conditions. Therefore, if the narrowing conditions are changed or lifted, images which had previously not been targets for comparative image observation will be immediately available for display.

As yet another modification, a configuration may be adopted wherein a user interface is provided that receives settings regarding a maximum number of thumbnail images to be displayed in an image window in the active state. In this case, the display control means displays a number of thumbnail images less than or equal to the set maximum number. Thereby, the displayed thumbnail images becoming too small and difficult to view due to the number thereof increasing can be prevented. Further, a configuration may be adopted wherein a user interface is provided that receives selection of thumbnail images to be displayed, and the display control means 62 displays only the selected thumbnail images, in the case that the number of selected thumbnail images exceeds the maximum value. Thereby, it becomes possible to display only thumbnail images that users desire to view.

Figure 14:
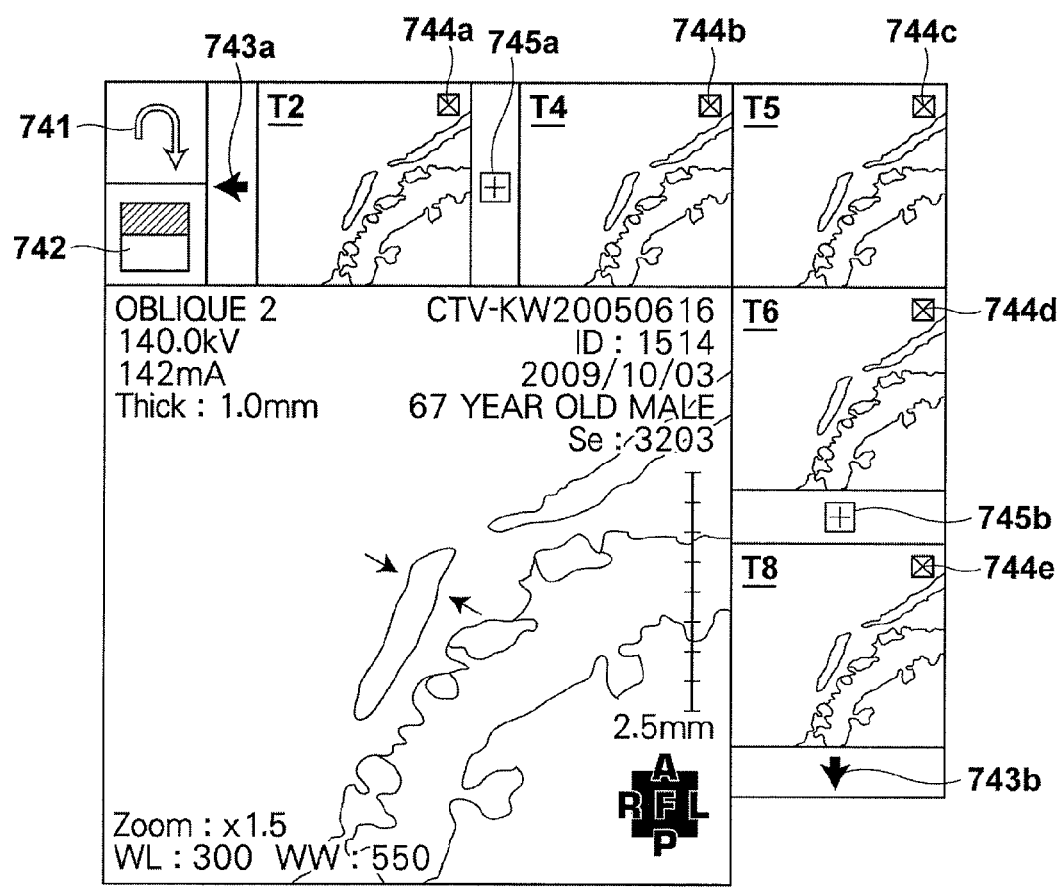
FIG. 14 is a diagram that illustrates an example of display of an image window in an active state.

FIG. 14 is a diagram that illustrates a modification to the display of an image window in an active state of FIG. 4A. A user interface as described below is realized by control exerted by the display control means 62.

As illustrated in FIG. 14, in the present modification, "Cancel Display" buttons 744a through 744e are provided in each of thumbnail images T2 through T8 within the temporary display region. If the "Cancel Display" button of a thumbnail image that a user does not wish to have displayed is clicked, the thumbnail image is no longer displayed. Thereby, it becomes possible for users to cause selective display of only thumbnail images that they wish to view. Note that the position at which the "Cancel Display" button is provided is not limited to the example illustrated in FIG. 14. Another preferred display position for the "Cancel Display" button is the upper left corners of the thumbnail images.

Icons 745a and 745b are icons that represent that thumbnail images T3 and T7 are no longer being displayed. As described above, if the "Cancel Display" buttons of thumbnail images are clicked, the thumbnail images are no longer displayed, and an icon that represents a cancelled display state is displayed at the position of the non displayed thumbnail image. By adopting this configuration, users will be enabled to be aware of the presence of the thumbnail images that were set not to be displayed, thereby preventing necessary images from being overlooked. Here, the sizes of thumbnail images that remain displayed are automatically adjusted, based on the lengths of the vertical and horizontal sides of the temporary display regions and the number of remaining thumbnail images, accompanying the decrease in the number of thumbnail images which are to be displayed. Conversely, if the non display state icon 754*a* is clicked, the thumbnail image T3 is displayed again at its original position. At this time, the sizes of thumbnail images that remain displayed are automatically adjusted, based on the lengths of the vertical and horizontal sides of the temporary display regions and the number of thumbnail images, accompanying the increase in the number of thumbnail images which are to be displayed. Note that the shape of the non display state icon is not limited to that shown in FIG. 14, and it is preferable for the shape icon to conserve as much space as possible. For example, the thumbnail images T2 and T4 may be displayed such that they contact each other, with the boundary therebetween being of a color, a line type, or having a thickness different form the boundaries among sequential thumbnail images to be displayed. The non display state of the thumbnail image T3 may be represented in this manner.

In addition, FIG. 14 illustrates a state in which not all thumbnail images T1 through T10, which are to be displayed, are displayed. Here, by clicking on the arrow icon 743A, the thumbnail images which are displayed are updated such that they slide toward the right. That is, the thumbnail images which are displayed are updated to T1, T2, T4, T5, and T6 from T2, T4, T5, T6, and T8, thumbnail image T1, which had not been displayed previously, appears in the image window, and thumbnail image T8 is no longer displayed. Similarly, if arrow icon 743*b* is clicked once in the state illustrated in FIG. 14, the thumbnail images which are displayed are updated such that they slide upward, that is, updated to T4, T5, T6, T8, and T9 from T2, T4, T5, T6, and T8. Thumbnail mage T9, which had not been displayed previously, appears in the image window, and thumbnail image T2 is no longer displayed. Further, if the arrow icon 743*b* is clicked once more, thumbnail image T10 will appear in the image window, and thumbnail image T4 will no longer be displayed.

If icon button 741 is clicked, the display of the thumbnail images will return to the initial state.

If icon button 742 is clicked, the display control means 62 opens another image window, and displays a catalog of images for observation corresponding to the thumbnail images which are currently being displayed. By adopting this configuration, detailed comparative image observation can be performed using images for observation of large sizes, even in cases that the sizes of individual thumbnail images are too small and cause comparative image observation to become difficult, by the catalog of corresponding images for observation being displayed.

Figure 15:
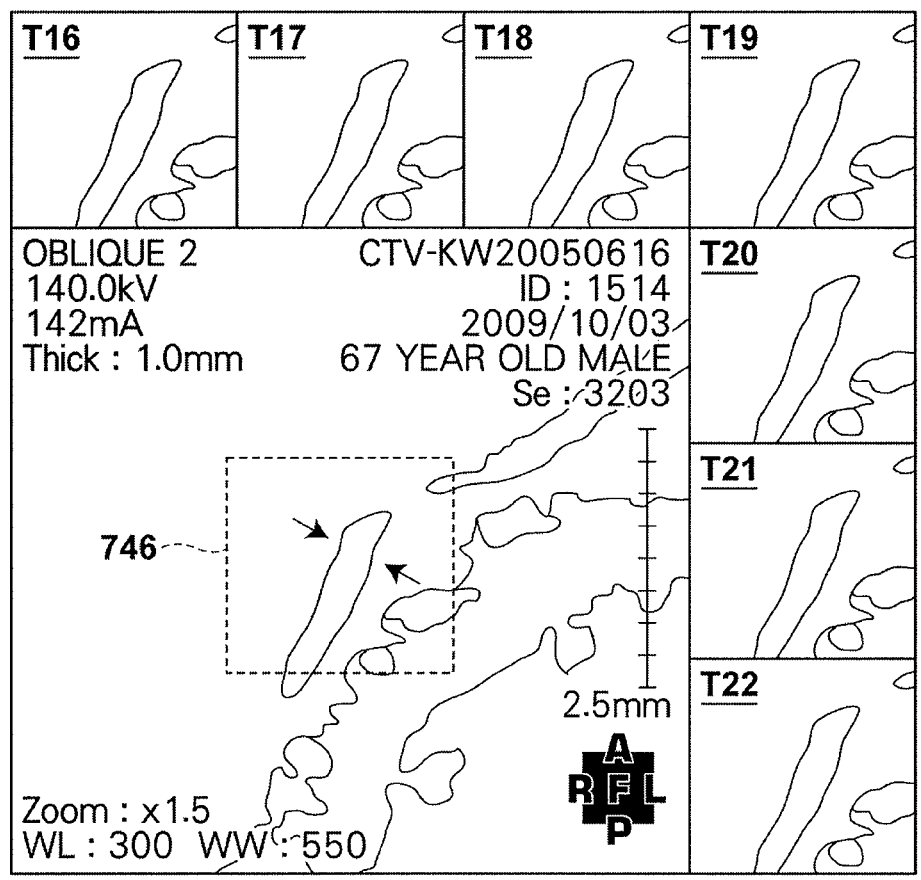
FIG. 15 is a diagram that illustrates another example of display of an image window in an active state.

FIG. 15 is a diagram that illustrates a preferred modification of the present invention, related to coordinated updating of display of an image for observation and thumbnail images. In this configuration, users are enabled to set a frame 746 that represents a region to be cut out from within an image for observation displayed in an image window in the active state, by a click and drag operation of a mouse, as illustrated in FIG. 15. When the frame 746 is set, the image generating means 63 generates thumbnail images that represent portions of the images for observation corresponding thereto that correspond to the specified cutout region. Then, the display control means 62 updates the display of the thumbnail images to the newly generated thumbnail images, while maintaining the display of the frame 746 within the image for observation. Note that the cutout region within each of the images for observation may be determined based on correspondent relationships among coordinate values of the images. Alternatively, in the case that the images represent a tubular structure, the cutout region may be determined based on the distance (length along a pathway) from the starting point of the pathway, employing pathway analysis results of the structure.

In the above embodiment, a thumbnail image that corresponds to the image for observation being displayed in the constant display region is also displayed in the temporary display region. Alternatively, a configuration may be considered, in which thumbnail images that correspond to images for observation being displayed in the constant display region are not displayed in the temporary display region. In this configuration, display may be controlled such that when an operation to specify a thumbnail image is performed, an image for and the specified thumbnail image are switched.

In addition, in the above embodiment, the thumbnail images are displayed in the temporary display regions that appear only when an image window is activated. Alternatively, a configuration may be considered, in which the temporary display regions are not provided, and thumbnail images are displayed within the existing frame of an activated image window. In this case, there is a problem that the image for observation within an activated window becomes difficult to observer. At the same time, however, such a configuration provides the advantageous effect that inactive image windows about the periphery of the active image window will not be obscured by thumbnail images.

Note that in FIG. 8 and the description corresponding thereto, only image generating sections which are necessary to realize the layout illustrated in FIG. 2A and FIG. 2B were described. However, as described previously, the layout of the diagnosis screen differs according to the target of diagnosis (particularly the contents of images to be displayed). For this reason, it is preferable for the image generating means 63 to be further equipped with a great number of program modules in addition to those listed in the aforementioned description. Examples of such program modules include those that generate MIP (Maximum Intensity Projection) images, bulls eye images, virtual endoscope images, etc. It is preferable for the image generating means 63 to select and utilize the program modules according to selected functions (targets of diagnosis).

In FIG. 8 and the description corresponding thereto, the thinning section and the image generating sections were described as separate processing sections. However, it is possible to perform the thinning process and an image generating process (a projection process, for example) simultaneously. Alternatively, the image generating sections may generate the images for observation in various observation formats, and the thumbnail images may be generated by thinning the generated images for observation.

Further, a positioning process that matches the position of a subject within each set of volume data may be performed as a preliminary process by the image generating means 63. By adopting this configuration, positional shifts of the subject among each set of volume data caused by body movements due to respiration, differences in body positions during imaging, differences in imaged ranges among imaging operations, and the like, can be corrected. Thereby, corresponding positions of the subject can be observed when performing comparative image observation of the images for observation and the thumbnail images.

Known nonrigid registration techniques or the like may be employed as the specific positioning method. Examples of such techniques include that in which two corresponding points are specified by users, and that in which positioning is performed based on image contrast, without using any landmarks (for details, refer to Japanese Unexamined Patent Publication No. 2005-028121, and D. Rueckert et al., "Nonrigid Registration Using Free-Form Deformations: Application to Breast MR Images", IEEE Transactions on Medical Imaging, Vol. 18, No. 8, pp. 712-721, 1999). Alternatively, the method proposed in U.S. Patent Application Publication No. 20090232378 filed by the present applicant, in which an automatic discrimination process of imaged portions within each slice of volume data is applied to perform positioning of the boundaries of different imaged portions among sets of volume data, may be applied.

In the case that the target of diagnosis is the coronary arteries, positioning is also possible by matching the tree structure data of coronary arteries which are extracted from each set of volume data.

Specifically, first, a region corresponding to the heart (hereinafter, referred to as "cardiac region") is extracted from each set of volume data by a predetermined algorithm. Next, a rectangular parallelepiped region that includes the cardiac region is set as a search range. Then, linear structures which are included in the search range are searched for based on a predetermined algorithm. Further, points which are estimated to be points along the cores of coronary arteries are detected, based on the linear structures detected by the search. In the following description, the points which are estimated to be points along the cores of coronary arteries will be referred to as candidate points or nodes. The search for the linear structures is performed by calculating unique values of a 3×3 Hessian matrix for each local region within the search range. In regions that include linear structures, one of the three unique values of the Hessian matrix becomes a value close to zero, while the other two values will be relatively greater values. In addition, the unique vector that corresponds to the unique value close to zero indicates the direction of the main axis of the linear structures. In the coronary artery extracting process 14, this relationship is utilized to judge likelihoods of being linear structures based on the unique values of a Hessian matrix for each local region. In local regions in which linear structures are discriminated, the center points thereof are detected as candidate points. Next, the candidate points which are detected by the search are linked based on a predetermined algorithm. Thereby, tree structures constituted by the candidate points and blood vessel branches (edges) that connect the candidate points are constructed. The coordinate data of the detected plurality of candidate points and vector data that represent the directions of the blood vessel branches are stored in the memory, along with identifiers for the candidate points and the blood vessel branches. Next, the shapes of the coronary arteries are discriminated in detail based on the values of the surrounding voxels (CT values) for each detected candidate point. More specifically, the outlines (the outer walls of the blood vessels) of the coronary arteries are discriminated within cross sections perpendicular to the pathways of the coronary arteries. The discrimination of shapes is performed employing a known segmentation method, such as the Graph Cuts method. The above processes generate data necessary to specify the extracted coronary artery regions.

Here, in regions of the subject at which changes do not occur over time, substantially the same points are detected as candidate points in each set of volume data. Therefore, the tree structures can be matched among sets of volume data (graph matching) by using the candidate points within regions at which changes do not occur over time. That is, the degrees of similarity for main nodes are calculated based on a predetermined evaluation function, and the candidate points having the highest degrees of similarity are correlated with each other. Then, the correspondent relationships among the other candidate points are estimated based on the correspondent relationships among the main nodes of the tree structure. By this method, points which are the same anatomically can be correlated with each other, even if the shapes of the coronary artery regions extracted from sets of volume data are different. Note that various other methods for correlating anatomic structures by graph matching have been proposed, as disclosed in U.S. Pat. No. 7,646,903.

Note that the positioning process will yield the same advantageous effects if it is performed respect to each generated image for observation, each thumbnail image, and each observation format, instead of as a preliminary process. However, the number of positioning processes will increase in this case, and therefore it is preferable to performing the positioning process as a preliminary process, from the viewpoint of processing efficiency.

The above embodiment has been described as a client/server system. Alternatively, a single computer may function as the volume data storage means, the volume data selecting means, the image generating means, the image window control means, and the display control means. With respect to devices that constitute the system, such as the input device and the display, various known devices may be employed. For example, a joystick may be substituted for the mouse, and a touch panel may be substituted for the display.

As described above, the present invention is not limited to the embodiment described above. Various changes and modifications are possible, as long as they do not stray from the spirit of the invention. In addition, the present invention is not limited to assisting diagnosis of coronary arteries, and may be employed to assist diagnosis of various living tissue. Further, the present invention is not limited to assisting diagnosis of living organisms, and may be utilized for periodic inspections to assess deterioration of machinery and the like.

What is claimed is:

1. A diagnosis assisting system, comprising:

volume data storage means, for storing a plurality of sets of volume data, obtained by imaging at least one subject on different imaging dates/times, in a predetermined storage device, correlated with subject identifying data and imaging date/time data;

volume data selecting means, for selecting at least two sets of volume data correlated with subject identifying data that represents a specified subject, from among the sets of volume data stored in the storage device;

image generating means, for generating a plurality of images for observation in different observation formats that represent the specified subject for each set of volume data selected by the volume data selecting means, for generating a plurality of thumbnail images corresponding to each of the images for observation, and for correlating the images for observation, the thumbnail images, and the imaging date/time data of the set of volume data corresponding thereto;

image window control means, for arranging a plurality of image windows, each of the plurality of image windows configured to be separately switchable between an active state and an inactive state, on a screen, and for controlling the switching from the active state and the inactive state; and display control means, for selecting images for observation which are correlated with imaging date/time data that represent a specified imaging date/time from among the images for observation generated by the image generating means, for displaying the selected images for observation in the image windows, for selecting thumbnail images having the same observation format as that of the image for observation which is displayed in the active image window from among the thumbnail images generated by the image generating means, and for displaying the selected thumbnail images within the active image window, wherein active and inactive windows of the plurality of windows are shown simultaneously, and the image window control means controls the active window, and each of the plurality of windows is correlated with a corresponding set of thumbnail images stored in memory, said set of thumbnails corresponding to an observation format for each respective image window of the plurality of windows, and only the set of thumbnails corresponding to a window among the plurality of windows set to the active state is displayed, and windows having the inactive state display a medical image according to respective observation format, without its respective corresponding set of thumbnails.

2. A diagnosis assisting system as defined in claim 1, wherein:
the image generating means generates an image for observation and a thumbnail image corresponding to a specified observation format, when an operation that requests a change in the observation format of an image for observation displayed in an active image window; and
the display control means updates the display to display the generated image for observation and the generated thumbnail image.

3. A diagnosis assisting system as defined in claim 2, wherein:
the image generating means generates a thumbnail image corresponding to a region which is to be cut out from an image for observation, when an operation that specifies a region to be cut out from an image for observation displayed in an active image window; and
the display control means displays the region to be cut out within the image for observation in a recognizable format, and updates the display to display the generated thumbnail image.

4. A diagnosis assisting system as defined in claim 1, wherein:
the image window control means arranges a plurality of image windows having one constant display region and at least one temporary display region on the screen, and controls each image window such that the temporary display regions appear on the screen only when the image window it belongs in is in an active state; and
the display control means causes the selected images for observation to be displayed in the constant display region of each image window, and displays the selected thumbnail images in the temporary display regions of an image window in the active state.

5. A diagnosis assisting system as defined in claim 4, wherein:
the display control means displays an image for observation within the constant display region of an active image window corresponding to a specified thumbnail image, when a first operation that specifies a thumbnail image within a temporary display region is detected.

6. A diagnosis assisting system as defined in claim 4, wherein:
the display control means replaces a specified thumbnail image within a temporary display region with an image for observation corresponding to the specified thumbnail image, when a second operation that specifies a thumbnail image within a temporary display region is detected.

7. A diagnosis assisting system as defined in claim 4, wherein:
the image window control means sets the temporary display regions based on the number of thumbnail images selected by the display control means.

8. A diagnosis assisting system as defined in claim 1, wherein:
the display control means receives settings regarding a maximum value for the number of thumbnail images to be displayed within an image window in the active state, and displays a number of thumbnail images less than or equal to the set maximum value.

9. A diagnosis assisting system as defined in claim 8, wherein:
the display control means receives selection of thumbnail images to be displayed, and displays only the selected thumbnail images, in the case that the number of selected thumbnail images exceeds the maximum value.

10. A diagnosis assisting system as defined in claim 1, wherein:
the display control means receives settings regarding whether each of the thumbnail images within an image window in the active state are to be displayed, and only displays thumbnail images which are set to be displayed.

11. A diagnosis assisting system as defined in claim 10, wherein:
the display control means displays positions at which thumbnail images, which have been set to not be displayed, had been displayed in a recognizable manner.

12. A diagnosis assisting system as defined in claim 1, wherein:
the display control means adds and displays at least a portion of the photography date represented by the photography date/time data correlated to each of the images for observation and/or the thumbnail images when displaying the images for observation and/or the thumbnail images.

13. A diagnosis assisting system as defined in claim 1, wherein:
the display control means displays a catalog of images for observation that correspond to thumbnail images which are displayed within an image window in the active state, in response to a predetermined operation by a user.

14. A diagnosis assisting system as defined in claim 1, wherein:
the volume data selecting means selects sets of volume data that satisfies first narrowing conditions for narrowing sets of volume data which are targets for selection.

15. A diagnosis assisting system as defined in claim 14, wherein:
the first narrowing conditions are those that narrow the volume data to be selected to volume data which were obtained by imaging within a predetermined period; and
the volume data selecting means selects sets of volume data that satisfy the first narrowing conditions, based on the imaging date/time data correlated with the volume data.

16. A diagnosis assisting system as defined in claim 14, wherein:
the sets of volume data stored in the storage device are further correlated with examination identifying data that identify each examination by which volume data were obtained;
the first narrowing conditions are those that narrow the volume data to be selected to volume data which were obtained by a predetermined number of recent examinations; and the volume data selecting means selects sets of volume data that satisfy the first narrowing conditions, based on the examination identifying data correlated with the volume data.

17. A diagnosis assisting system as defined in claim 14, wherein:
the sets of volume data stored in the storage device are further correlated with one of examination data that represent the examination during obtainment of the volume data and diagnostic result data that represent the results of diagnosis;
the first narrowing conditions are those that narrow volume data to be selected to volume data which are correlated with one of a specific examination and a specific diagnostic result; and
the volume data selecting means selects sets of volume data that satisfy the first narrowing conditions, based on the examination data and the diagnostic result data correlated with the volume data.

18. A diagnosis assisting system as defined in claim 1, wherein:
the display control means selects thumbnail images that further satisfy second narrowing conditions, and causes the selected thumbnail images to be displayed within an image window in the active state.

19. A diagnosis assisting system as defined in claim 18, wherein:
the second narrowing conditions are those that narrow the thumbnail images to be selected to thumbnail images which were obtained by imaging within a predetermined period; and
the display control means selects thumbnail images that satisfy the second narrowing conditions, based on the imaging date/time data correlated with the thumbnail images.

20. A diagnosis assisting system as defined in claim 18, wherein:
the sets of volume data stored in the storage device are further correlated with examination identifying data that identify each examination by which volume data were obtained;
the image generating means correlates the examination identifying data, which are correlated to the volume data, to the images for observation and the thumbnail images generated therefrom;
the second narrowing conditions are those that narrow the thumbnail images to be selected to be those which are generated from volume data which were obtained by a predetermined number of recent examinations; and
the display control means selects and displays thumbnail images that satisfy the second narrowing conditions, based on the examination identifying data correlated with the thumbnail images.

21. A diagnosis assisting system as defined in claim 18, wherein:
the sets of volume data stored in the storage device are further correlated with one of examination data that represent the examination during obtainment of the volume data and diagnostic result data that represent the results of diagnosis;
the image generating means correlates the examination data and the diagnostic result data, which are correlated to the volume data, to the images for observation and the thumbnail images generated therefrom;

the second narrowing conditions are those that narrow volume data to be selected to volume data which are correlated with one of a specific examination and a specific diagnostic result; and
the display control means selects and displays thumbnail images that satisfy the second narrowing conditions, based on the examination data and the diagnostic result data correlated with the thumbnail images.

22. A diagnosis assisting system as defined in claim 1, wherein:
the image generating means further performs a positioning process such that the positions of subjects within the images for observation and the thumbnail images which are generated from each set of volume data are matched among the sets of volume data.

23. A diagnosis assisting system as defined in claim 1, wherein:
the image window control means changes the layout of the plurality of image windows in response to predetermined user operations.

24. The system of claim 1, wherein active and inactive windows of the plurality of windows are shown simultaneously, and the image window control means controls the active window.

25. A non-transitory computer readable recording medium having recorded therein a program that causes at least one computer to function as:
volume data storage means, for storing a plurality of sets of volume data, obtained by imaging at least one subject on different imaging dates/times, in a predetermined storage device, correlated with subject identifying data and imaging date/time data;
volume data selecting means, for selecting at least two sets of volume data correlated with subject identifying data that represents a specified subject, from among the sets of volume data stored in the storage device;
image generating means, for generating a plurality of images for observation in different observation formats that represent the specified subject for each set of volume data selected by the volume data selecting means, for generating a plurality of thumbnail images corresponding to each of the images for observation, and for correlating the images for observation, the thumbnail images, and the imaging date/time data of the set of volume data corresponding thereto;
image window control means, for arranging a plurality of image windows, each of the plurality of image windows configured to be separately switchable between an active state and an inactive state, on a screen, and for controlling the switching from the active state and the inactive state; and
display control means, for selecting images for observation which are correlated with imaging date/time data that represent a specified imaging date/time from among the images for observation generated by the image generating means, for displaying the selected images for observation in the image windows, for selecting thumbnail images having the same observation format as that of the image for observation which is displayed in the active image window from among the thumbnail images generated by the image generating means, and for displaying the selected thumbnail images within the active image window,
wherein active and inactive windows of the plurality of windows are shown simultaneously, and the image window control means controls the active window, and each of the plurality of windows is correlated with a corresponding set of thumbnail images stored in memory, said set of thumbnails corresponding to an observation format for each respective image window of the plurality of windows, and only the set of thumbnails corresponding to a window among the plurality of windows set to the active state is displayed, and windows having the inactive state display a medical image according to respective observation format, without its respective corresponding set of thumbnails.

26. A diagnosis assisting method that causes at least one computer to execute:

a volume data storage process, for storing a plurality of sets of volume data, obtained by imaging at least one subject on different imaging dates/times, in a predetermined storage device, correlated with subject identifying data and imaging date/time data;

a volume data selecting process, for selecting at least two sets of volume data correlated with subject identifying data that represents a specified subject, from among the sets of volume data stored in the storage device;

an image generating process, for generating a plurality of images for observation in different observation formats that represent the specified subject for each set of volume data selected by the volume data selecting process, for generating a plurality of thumbnail images corresponding to each of the images for observation, and for correlating the images for observation, the thumbnail images, and the imaging date/time data of the set of volume data corresponding thereto;

an image window control process, for arranging a plurality of image windows, each of the plurality of image windows configured to be separately switchable between an active state and an inactive state, on a screen, and for controlling the switching from the active state and the inactive state; and a display control process, for selecting images for observation which are correlated with imaging date/time data that represent a specified imaging date/time from among the images for observation generated by the image generating means, for displaying the selected images for observation in the image windows, for selecting thumbnail images having the same observation format as that of the image for observation which is displayed in the active image window from among the thumbnail images generated by the image generating means, and for displaying the selected thumbnail images within the active image window, wherein active and inactive windows of the plurality of windows are shown simultaneously, and the image window control means controls the active window, and each of the plurality of windows is correlated with a corresponding set of thumbnail images stored in memory, said set of thumbnails corresponding to an observation format for each respective image window of the plurality of windows, and only the set of thumbnails corresponding to a window among the plurality of windows set to the active state is displayed, and windows having the inactive state display a medical image according to respective observation format, without its respective corresponding set of thumbnails.

* * * * *